(12) United States Patent
Masaki et al.

(10) Patent No.: US 7,759,504 B2
(45) Date of Patent: *Jul. 20, 2010

(54) TRIARYLAMINE DERIVATIVE

(75) Inventors: Tomohito Masaki, Kanagawa (JP);
Keizo Kimura, Kanagawa (JP); Osamu Uchida, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/100,940

(22) Filed: Apr. 10, 2008

(65) Prior Publication Data

US 2008/0255387 A1    Oct. 16, 2008

(30) Foreign Application Priority Data

Apr. 13, 2007   (JP)   .............................. 2007-106372

(51) Int. Cl.
*C07C 50/04*    (2006.01)
*C07C 257/00*   (2006.01)
*G03C 1/00*     (2006.01)

(52) U.S. Cl. ..................... 552/301; 564/270; 430/270.1

(58) Field of Classification Search ................. 564/270; 552/301; 430/270

See application file for complete search history.

(56) References Cited

U.S. PATENT DOCUMENTS

| 6,255,031 | B1 | 7/2001 | Yao et al. |
| 2005/0113474 | A1 | 5/2005 | Kropp et al. |
| 2005/0148786 | A1 | 7/2005 | Ikeda et al. |
| 2008/0255387 | A1 | 10/2008 | Masaki et al. |

FOREIGN PATENT DOCUMENTS

| JP | 4-146905 A | 5/1992 |
| JP | 5-142811 A | 6/1993 |
| JP | 2002-82219 A | 3/2002 |
| JP | 2005-325292 A | 11/2005 |
| JP | 2005-336150 A | 12/2005 |
| JP | 2006-143674 A | 6/2006 |
| WO | WO 2005/037940 | * 4/2005 |

OTHER PUBLICATIONS

Neunhoeffer et al., "Der Deutchen Chemischen Gesellschaft" vol. 92, pp. 245-251 (1959).
F. Ritschl, Spectrochimica Acta, vol. 23, pp. 655-675 (1967).

* cited by examiner

*Primary Examiner*—Porfirio Nazario-Gonzalez
*Assistant Examiner*—Yate' K Cutliff
(74) *Attorney, Agent, or Firm*—Birch, Stewart, Kolasch & Birch, LLP

(57) ABSTRACT

A triarylamine derivative is represented by the following Formula (I). In Formula (I): $R^{111}$, $R^{112}$, $R^{121}$ and $R^{122}$ each independently represent a hydrogen atom, an aliphatic group or an aromatic group, $R^{113}$, $R^{114}$, $R^{115}$, $R^{116}$, $R^{123}$, $R^{124}$, $R^{125}$ and $R^{126}$ each independently represent a hydrogen atom or a substituent, provided that at least one pair among $R^{111}$ and $R^{121}$, $R^{112}$ and $R^{122}$, $R^{113}$ and $R^{123}$, $R^{114}$ and $R^{124}$, $R^{115}$ and $R^{125}$ and $R^{116}$ and $R^{126}$ includes two different groups; at least one ring may be formed by mutual bonding in at least one pair among $R^{111}$ and $R^{112}$, $R^{111}$ and $R^{114}$, $R^{113}$ and $R^{114}$, $R^{113}$ and $R^{123}$, $R^{123}$ and $R^{124}$, $R^{121}$ and $R^{124}$, $R^{121}$ and $R^{122}$, and two $R^{116}$s which are respectively bound to different phenyl groups; $X^{m-}$ represents an m-valent anion; m and n represent 1 or 2; and a product of m and n is 2.

Formula (I)

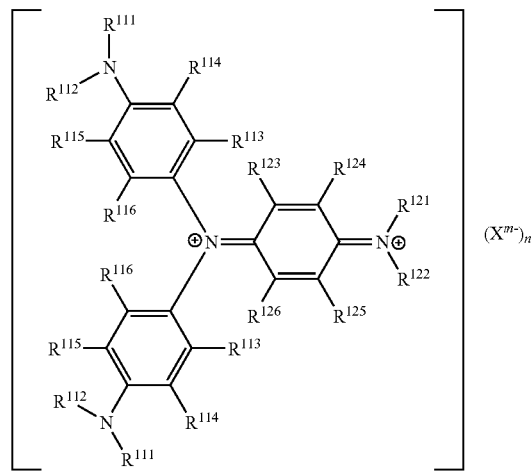

14 Claims, No Drawings

TRIARYLAMINE DERIVATIVE

CROSS-REFERENCE TO RELATED APPLICATION

This application claims priority under 35 USC 119 from Japanese patent Application No. 2007-106372, the disclosure of which is incorporated by reference herein.

BACKGROUND OF THE INVENTION

1. Field of the Invention

The present invention relates to a triarylamine derivative having absorption in a near infrared region.

2. Description of the Related Art

Conventionally, a diimmonium compound which is one kind of triarylamine derivative has been widely known as a near infrared absorbing compound (see, for example, Japanese Patent Application Laid Open (JP-A) No. 4-146905; JP-A No. 5-142811; JP-A No. 2002-82219; "Der Deutschen Chemischen Gesellschaft" vol. 92, pp. 245-251 (1959); and "Spectrochemica Acta" vol. 23, pp. 655-675 (1967)), and has been widely used in photopolymerization initiators, and electrophotographic photoreceptors. However, generally, the diimmonium compound as a near infrared absorbing compound still has a problem in wet heat resistance and solubility. On the other hand, it is known that wet heat resistance and solubility can be improved by changing an anion which is a counterion, or changing an alkyl group bound to an aminophenyl group of a diimmonium ion (see, for example, JP-A No. 2005-325292, JP-A No. 2005-336150 and JP-A No. 2006-143674).

In addition, it is known that heat resistance is improved by using an antimony hexafluoride ion as a counterion of the diimmonium compound. However, since a compound containing antimony is a deleterious substance, in view of loading on the environment, a high heat resistant diimmonium compound containing no antimony is desired in the industrial field. As a means to solve this problem, a diimmonium compound having a counterion such as a perchlorate ion or a hexafluorophosphate ion is known.

SUMMARY OF THE INVENTION

However, conventional diimmonium compounds are hardly satisfactory in wet heat resistance and solubility even when a perchlorate ion or a hexafluorophosphate ion is used as a counterion. In addition, it was difficult to set a maximum absorption wavelength of the diimmonium compound to a wavelength.

An aspect of the present invention provides a triarylamine derivative represented by the following Formula (I):

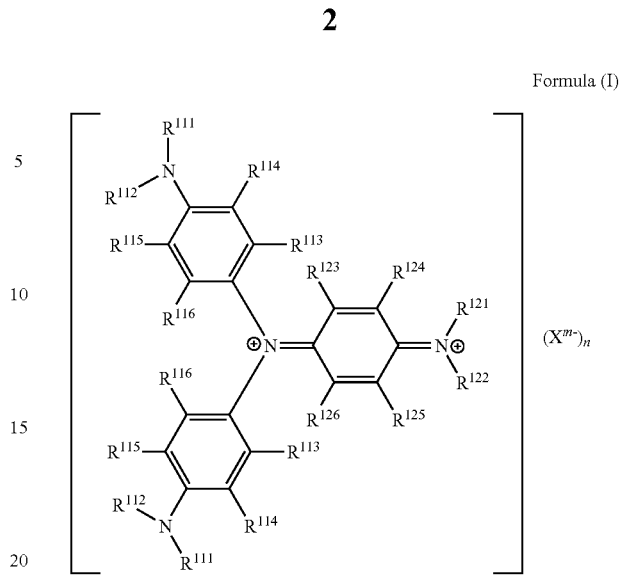

Formula (I)

wherein, in Formula (I): $R^{111}$, $R^{112}$, $R^{121}$ and $R^{122}$ each independently represent a hydrogen atom, an aliphatic group or an aromatic group, $R^{113}$, $R^{114}$, $R^{115}$, $R^{116}$, $R^{123}$, $R^{124}$, $R^{125}$ and $R^{126}$ each independently represent a hydrogen atom or a substituent, provided that at least one pair among $R^{111}$ and $R^{121}$, $R^{112}$ and $R^{122}$, $R^{113}$ and $R^{123}$, $R^{114}$ and $R^{124}$, $R^{115}$ and $R^{125}$, and $R^{116}$ and $R^{126}$ includes two different groups; at least one ring may be formed by mutual bonding in at least one pair among $R^{111}$ and $R^{112}$, $R^{111}$ and $R^{114}$, $R^{113}$ and $R^{114}$, $R^{113}$ and $R^{123}$, $R^{123}$ and $R^{124}$, $R^{121}$ and $R^{124}$, $R^{121}$ and $R^{122}$, and two $R^{116}$s which are respectively bound to different phenyl groups; $X^{m-}$ represents an m-valent anion; m and n represent 1 or 2; and a product of m and n is 2.

DETAILED DESCRIPTION OF THE INVENTION

The triarylamine derivative according to the present invention is represented by the following Formula (I). The triarylamine derivative represented by the following Formula (I) or a tautomer thereof is a near infrared absorbing diimmonium compound which is good in light resistance, wet heat resistance and solubility.

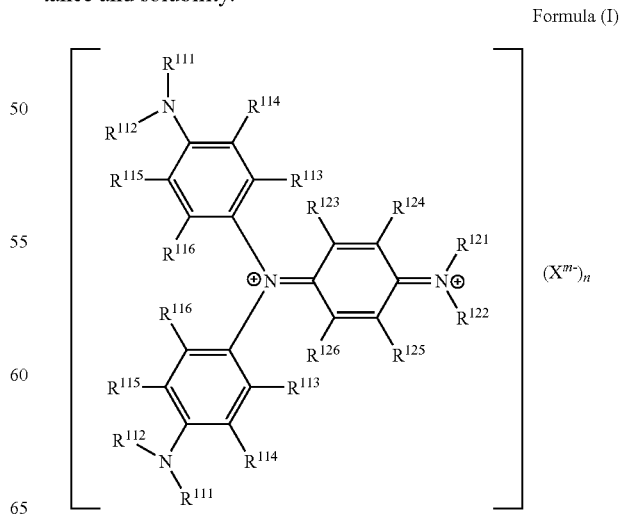

Formula (I)

In Formula (I), $R^{111}$, $R^{112}$, $R^{121}$ and $R^{122}$ each independently represent a hydrogen atom, an aliphatic group or an aromatic group, and $R^{113}$, $R^{114}$, $R^{115}$, $R^{116}$, $R^{123}$, $R^{124}$, $R^{125}$ and $R^{126}$ each independently represent a hydrogen atom or a substituent, provided that combinations of $R^{111}$ and $R^{121}$, $R^{112}$ and $R^{122}$, $R^{113}$ and $R^{123}$, $R^{114}$ and $R^{124}$, $R^{115}$ and $R^{125}$, and $R^{116}$ and $R^{126}$ include at least one combination that is composed of groups that are different from each other. In this proviso, the notion of "group" includes a hydrogen atom. $R^{111}$ and $R^{112}$ may be connected to each other to form a ring. $R^{111}$ and $R^{114}$ may be connected to each other to form a ring. $R^{113}$ and $R^{114}$ may be connected to each other to form a ring. $R^{113}$ and $R^{123}$ may be connected to each other to form a ring. $R^{123}$ and $R^{124}$ may be connected to each other to form a ring. $R^{121}$ and $R^{124}$ may be connected to each other to form a ring. $R^{121}$ and $R^{122}$ may be connected to each other to form a ring. The two $R^{116}$s which are bound to different phenyl groups may be connected to each other to form a ring $X^{m-}$ represents a m-valent anion, m and n each independently represent 1 or 2, provided that the product of m and n is 2.

In the invention, the aliphatic group means an alkyl group, a substituted alkyl group, an alkenyl group, a substituted alkenyl group, an alkynyl group, a substituted alkynyl group, an aralkyl group or a substituted aralkyl group. The alkyl group may be branched, and may form a ring. The number of the carbon atoms in the alkyl group is preferably from 1 to 20, more preferably from 1 to 18. The scope of the alkyl moiety of a substituted alkyl group is the same as the above definition of an alkyl group. Specific examples of alkyl groups include a methyl group, an ethyl group, a n-propyl group, an isopropyl group, a t-butyl group, a n-octyl group, an eicosyl group, a 2-chloroethyl group, a 2-cyanoethyl group, a 2-ethylhexyl group, a cyclohexyl group, a cyclopentyl group, a 4-n-dodecyl cyclohexyl group, a bicyclo[1.2.2]heptan-2-yl group, and a bicyclo[2.2.2]octan-3-yl group.

The alkenyl group may be branched, and may form a ring. The number of the carbon atoms in the alkenyl group is preferably from 2 to 20, further preferably from 2 to 18. The scope of the alkenyl moiety of a substituted alkenyl group is the same as the above definition of an alkenyl group. Specific examples of alkenyl groups include a vinyl group, an allyl group, a prenyl group, a geranyl group, an oleyl group, a 2-cyclopenten-1-yl group, a 2-cyclohexen-1-yl group, a bicyclo[2.2.1]hept-2-en-1-yl group, and a bicyclo[2.2.2]oct-2-en-4-yl group.

The alkynyl group may be branched, and may form a ring. The number of the carbon atoms in the alkynyl group is preferably from 2 to 20, more preferably from 2 to 18. The scope of the alkynyl moiety of a substituted alkynyl group is the same as the above definition of an alkynyl group. Specific examples of alkynyl groups include an ethynyl group, a propargyl group, and a trimethylsilylethynyl group.

The scope of the alkyl moiety of an aralkyl group or a substituted aralkyl group is the same as the above definition of an alkyl group. The scope of the aryl moiety of an aralkyl group or a substituted aralkyl group is the same as the definition of an aryl group described below. Specific examples of aralkyl groups include a benzyl group and a phenylethyl group.

Examples of a substituent on the alkyl moiety of a substituted alkyl group, a substituted alkenyl group, a substituted alkynyl group or a substituted aralkyl group include the following substituents:

a halogen atom (e.g. a fluorine atom, a chlorine atom, a bromine atom, an iodine atom);

an alkyl group [a straight-chain, branched or cyclic, substituted or unsubstituted alkyl group, wherein the scope of this alkyl group includes an alkyl group (preferably, an alkyl group having 1 to 30 carbon atoms, such as a methyl group, an ethyl group, a n-propyl group, an isopropyl group, a t-butyl group, a n-octyl group, an eicosyl group, a 2-chloroethyl group, a 2-cyanoethyl group, or a 2-ethylhexyl group), a cycloalkyl group (preferably, a substituted or unsubstituted cycloalkyl group having a 3 to 30 carbon atoms, such as a cyclohexyl group, a cyclopentyl group, or a 4-n-dodecylcyclohexyl group), a bicycloalkyl group (preferably, a substituted or unsubstituted bicycloalkyl group having 5 to 30 carbon atoms, which is a monovalent group obtained by removing one hydrogen atom from a bicycloalkane having 5 to 30 carbon atoms, such as a bicyclo[1.2.2]heptan-2-yl group or a bicyclo[2.2.2]octan-3-yl group), and an alkyl group having three or more cyclic structures, for example a tricyclo structure; alkyl groups in substituents described below (e.g. alkyl groups in alkylthio groups) are alkyl groups of the same concept];

an alkenyl group [a straight-chain, branched or cyclic, substituted or unsubstituted alkenyl group, wherein the scope of this alkenyl group includes an alkenyl group (preferably, a substituted or unsubstituted alkenyl group having 2 to 30 carbon atoms, such as a vinyl group, an allyl group, a prenyl group, a geranyl group, or an oleyl group), a cycloalkenyl group (preferably a substituted or unsubstituted cycloalkenyl group having 3 to 30 carbon atoms, which is a monovalent group obtained by removing one hydrogen atom from a cycloalkene having 3 to 30 carbon atoms, such as a 2-cyclopenten-1-yl group or a 2-cyclohexen-1-yl group), and a bicycloalkenyl group (a substituted or unsubstituted bicycloalkenyl group, preferably a substituted or unsubstituted bicycloalkenyl group having 5 to 30 carbon atoms, which is a monovalent group obtained by removing one hydrogen atom from a bicycloalkene having one double bond, such as a bicyclo[2.2.1]hept-2-en-1-yl group or a bicyclo[2.2.2]oct-2-en-4-yl group)];

an alkynyl group (preferably, a substituted or unsubstituted alkynyl group having 2 to 30 carbon atoms, such as an ethynyl group, a propargyl group, or a trimethylsilylethynyl group);

an aryl group (preferably, a substituted or unsubstituted aryl group having 6 to 30 carbon atoms, such as a phenyl group, a p-tolyl group, a naphthyl group, a m-chlorophenyl group, or an o-hexadecanoylaminophenyl group);

a heterocyclic group (preferably a monovalent group obtained by removing one hydrogen atom from a 5- or 6-membered, substituted or unsubstituted, aromatic or non-aromatic heterocyclic compound, more preferably a 5- or 6-membered aromatic heterocyclic group having 3 to 30 carbon atoms, such as a 2-furyl group, a 2-thienyl group, a 2-pyrimidinyl group, or a 2-benzothiazolyl group);

a cyano group;

a hydroxy group;

a nitro group;

a carboxy group;

an alkoxy group (preferably, a substituted or unsubstituted alkoxy group having 1 to 30 carbon atoms, such as a methoxy group, an ethoxy group, an isopropyloxy group, a t-butoxy group, a n-octyloxy group, or a 2-methoxyethoxy group);

an aryloxy group (preferably, a substituted or unsubstituted aryloxy group having 6 to 30 carbon atoms, such as a phenoxy group, a 2-methylphenoxy group, a 4-t-butylphenoxy group, a 3-nitrophenoxy group, or a 2-tetradecanoylaminophenoxy group);

a silyloxy group (preferably, a silyloxy group having 3 to 20 carbon atoms, such as a trimethylsilyloxy group or a t-butyldimethylsilyloxy group);

a heterocyclic oxy group (preferably, a substituted or unsubstituted heterocyclic oxy group having 2 to 30 carbon atoms, a 1-phenyltetrazol-5-oxy group, or a 2-tetrahydropyranyloxy group);

an acyloxy group (preferably, a formyloxy group, a substituted or unsubstituted alkylcarbonyloxy group having 2 to 30 carbon atoms, or a substituted or unsubstituted arylcarbonyloxy group having 6 to 30 carbon atoms, such as a formyloxy group, an acetyloxy group, a pivaloyloxy group, a stearoyloxy group, a benzoyloxy group, or a p-methoxyphenylcarbonyloxy group);

a carbamoyloxy group (preferably, a substituted or unsubstituted carbamoyloxy group having 1 to 30 carbon atoms, such as a N,N-dimethylcarbainoyloxy group, a N,N-diethylcarbamoyloxy group, a morpholinocarbonyloxy group, a N,N-di-n-octylaminocarbonyloxy group, or a N-n-octylcarbamoyloxy group);

an alkoxycarbonyloxy group (preferably, a substituted or unsubstituted alkoxycarbonyloxy group having 2 to 30 carbon atoms, such as a methoxycarbonyloxy group, an ethoxycarbonyloxy group, a t-butoxycarbonyloxy group, or a n-octylcarbonyloxy group);

an aryloxycarbonyloxy group (preferably, a substituted or unsubstituted aryloxycarbonyloxy group having 7 to 30 carbon atoms, such as a phenoxycarbonyloxy group, a p-methoxyphenoxycarbonyloxy group, or a p-n-hexadecyloxyphenoxycarbonyloxy group);

an amino group (preferably, an amino group, a substituted or unsubstituted alkylamino group having 1 to 30 carbon atoms, or a substituted or unsubstituted anilino group having 6 to 30 carbon atoms, such as an amino group, a methylamino group, a dimethylamino group, an anilino group, a N-methylanilino group, or a diphenylamino group);

an acylamino group (preferably, a formylamino group, a substituted or unsubstituted alkylcarbonylamino group having 1 to 30 carbon atoms, or a substituted or unsubstituted arylcarbonylamino group having 6 to 30 carbon atoms, such as a formylamino group, an acetylamino group, a pivaloylamino group, a lauroylamino group, a benzoylamino group, or a 3,4,5-tri-n-octyloxyphenyl carbonylamino group);

an aminocarbonylamino group (preferably, a substituted or unsubstituted aminocarbonylamino group having 1 to 30 carbon atoms, such as a carbamoylamino group, a N,N-dimethylaminocarbonylamino group, a N,N-diethylaminocarbonylamino group, or a morpholinocarbonylamino group);

an alkoxycarbonylamino group (preferably, a substituted or unsubstituted alkoxycarbonylamino group having 2 to 30 carbon atoms, such as a methoxycarbonylamino group, an ethoxycarbonylamino group, a t-butoxycarbonylamino group, a n-octadecyloxycarbonylamino group, or a N-methyl-methoxycarbonylamino group);

an aryloxycarbonylamino group (preferably, a substituted or unsubstituted aryloxycarbonylamino group having 7 to 30 carbon atoms, such as a phenoxycarbonylamino group, a p-chlorophenoxycarbonylamino group, or a m-n-octyloxyphenoxycarbonylamino group);

a sulfamoylamino group (preferably, a substituted or unsubstituted sulfamoylamino group having 0 to 30 carbon atoms, such as a sulfamoylamino group, a N, N-dimethylaminosulfonylamino group, or a N-n-octylaminosulfonylamino group); an alkyl- or aryl-sulfonylamino group (preferably, a substituted or unsubstituted alkylsulfonylamino group having 1 to 30 carbon atoms or a substituted or unsubstituted arylsulfonylamino group having 6 to 30 carbon atoms, such as a methylsulfonylamino group, a butylsulfonylamino group, a phenylsulfonylamino group, a 2,3,5-trichlorophenylsulfonylamino group, or a p-methylphenylsulfonylamino group);

a mercapto group;

an alkylthio group (preferably, a substituted or unsubstituted alkylthio group having 1 to 30 carbon atoms, such as a methylthio group, an ethylthio group, or a n-hexadecylthio group);

an arylthio group (preferably, a substituted or unsubstituted arylthio group having 6 to 30 carbon atoms, such as a phenylthio group, a p-chlorophenylthio group, or a m-methoxyphenylthio group);

a heterocyclic thio group (preferably, a substituted or unsubstituted heterocyclic thio group having 2 to 30 carbon atoms, such as a 2-benzothiazolylthio group or a 1-phenyltetrazol-5-ylthio group);

a sulfamoyl group (preferably, a substituted or unsubstituted sulfamoyl group having 0 to 30 carbon atoms, such as a N-ethylsulfamoyl group, a N-(3-dodecyloxypropyl)sulfamoyl group, a N,N-dimethylsulfamoyl group, a N-acetylsulfamoyl group, a N-benzoylsulfamoyl group, or a N-(N'-phenylcarbamoyl)sulfamoyl group);

a sulfo group;

an alkyl- or aryl-sulfinyl group (preferably, a substituted or unsubstituted alkylsulfinyl group having 1 to 30 carbon atoms or a substituted or unsubstituted arylsulfinyl group having 6 to 30 carbon atoms, such as a methylsulfinyl group, an ethylsulfinyl group, a phenylsulfinyl group, or a p-methylphenylsulfinyl group);

an alkyl- or aryl-sulfonyl group (preferably, a substituted or unsubstituted alkylsulfonyl group having 1 to 30 carbon atoms or a substituted or unsubstituted arylsulfonyl group having 6 to 30 carbon atoms, such as a methylsulfonyl group, an ethylsulfonyl group, a phenylsulfonyl group, a p-methylphenylsulfonyl group), an acyl group (preferably, a formyl group, a substituted or unsubstituted alkylcarbonyl group having 2 to 30 carbon atoms, a substituted or unsubstituted arylcarbonyl group having 7 to 30 carbon atoms, or a substituted or unsubstituted heterocyclic carbonyl group having 4 to 30 carbon atoms and having a carbon atom bonded to the carbonyl group, such as an acetyl group, a pivaloyl group, a 2-chloroacetyl group, a stearoyl group, a benzoyl group, a p-n-octyloxyphenylcarbonyl group, a 2-pyridylcarbonyl group, or a 2-furylcarbonyl group);

an aryloxycarbonyl group (preferably, a substituted or unsubstituted aryloxycarbonyl group having 7 to 30 carbon atoms, such as a phenoxycarbonyl group, an o-chlorophenoxycarbonyl group, a m-nitrophenoxycarbonyl group, or a p-t-butylphenoxycarbonyl group);

an alkoxycarbonyl group (preferably, a substituted or unsubstituted alkoxycarbonyl group having 2 to 30 carbon atoms, such as a methoxycarbonyl group, an ethoxycarbonyl group, a t-butoxycarbonyl group, or a n-octadecyloxycarbonyl group);

a carbamoyl group (preferably, a substituted or unsubstituted carbamoyl group having 1 to 30 carbon atoms, such as a carbamoyl group, a N-methylcarbamoyl group, a N, N-dimethylcarbamoyl group, a N,N-di-n-octylcarbamoyl group, or a N-(methylsulfonyl)carbamoyl group);

aryl- and heterocyclyl-azo groups (preferably, a substituted or unsubstituted arylazo group having 6 to 30 carbon atoms or a substituted or unsubstituted heterocyclic azo group having 3 to 30 carbon atoms, such as a phenylazo group, a p-chlorophenylazo group, or a 5-ethylthio-1,3,4-thiadiazol-2-ylazo group);

an imido group (preferably, a N-succinimido group or a N-phthalimido group);

a phosphino group (preferably, a substituted or unsubstituted phosphino group having 2 to 30 carbon atoms, such as a dimethylphosphino group, a diphenylphosphino group, or a methylphenoxyphosphino group);

a phosphinyl group (preferably, a substituted or unsubstituted phosphinyl group having 2 to 30 carbon atoms, such as a phosphinyl group, a dioctyloxyphosphinyl group, or a diethoxyphosphinyl group);

a phosphinyloxy group (preferably, a substituted or unsubstituted phosphinyloxy group having 2 to 30 carbon atoms, such as a diphenoxyphosphinyloxy group or a dioctyloxyphosphinyloxy group);

a phosphinylamino group (preferably, a substituted or unsubstituted phosphinylamino group having 2 to 30 carbon atoms, such as a dimethoxyphosphinylamino group or a dimethylaminophosphinylamino group); and a silyl group (preferably, a substituted or unsubstituted silyl group having 3 to 30 carbon atoms, such as a trimethylsilyl group, a t-butyldimethylsilyl group, or a phenyldimethylsilyl group).

The scope of substituents also include those obtained by replacing hydrogen atoms in substituents having hydrogen atoms, among the above-mentioned substituents, with any of the above-mentioned substituents. Examples thereof include an alkylcarbonylaminosulfonyl group, an arylcarbonylaminosulfonyl group, an alkylsulfonylaminocarbonyl group, and an arylsulfonylaminocarbonyl group. More specific examples include a methylsulfonylaminocarbonyl group, a p-methylphenylsulfonylaminocarbonyl group, an acetylaminosulfonyl group, and a benzoylaminosulfonyl group.

When the aliphatic group is a substituted aralkyl group, examples of a substituent on the aryl moiety of the substituted aralkyl group are the same as examples of a substituent of a substituted aryl group described below.

In the invention, an aromatic group means an aryl group or a substituted aryl group. The aromatic group may be fused with an aliphatic ring, another aromatic ring or a heterocyclic ring. The number of the carbon atoms in the aryl group is preferably from 6 to 40, more preferably from 6 to 30, further preferably from 6 to 20. In particular, the aryl group is preferably a phenyl group or a naphthyl group, particularly preferably a phenyl group.

The above description on the aryl group applies also to the aryl moiety of a substituted aryl group. Examples of substituents of substituted aryl groups include the same substituents as those listed above as examples of substituents on the alkyl moieties of a substituted alkyl group, a substituted alkenyl group, a substituted alkynyl group and a substituted aralkyl group.

In the invention, $R^{111}$, $R^{112}$, $R^{121}$ and $R^{122}$ each independently represent preferably a hydrogen atom, a substituted or unsubstituted alkyl group, a substituted or unsubstituted alkenyl group, a substituted or unsubstituted alkynyl group, or a substituted or unsubstituted aryl group, more preferably a hydrogen atom, a substituted or unsubstituted alkyl group having a total carbon number of from 1 to 20, a substituted or unsubstituted alkenyl group having a total carbon number of from 2 to 20, a substituted or unsubstituted alkynyl group having a total carbon number of from 2 to 20, or a substituted or unsubstituted aryl group having a total carbon number of from 6 to 20, still more preferably a substituted or unsubstituted alkyl group having a total carbon number of from 1 to 10, a substituted or unsubstituted alkenyl group having a total carbon number of from 2 to 10, or a substituted or unsubstituted aryl group having a total carbon number of from 6 to 10, further preferably a substituted or unsubstituted alkyl group having a total carbon number of from 1 to 8, or a substituted or unsubstituted aryl group having a total carbon number of from 6 to 8, most preferably a substituted or unsubstituted alkyl group having a total carbon number of from 2 to 6.

$R^{113}$, $R^{114}$, $R^{115}$, $R^{116}$, $R^{123}$, $R^{124}$, $R^{125}$ and $R^{126}$ each independently represent preferably a hydrogen atom, a halogen atom, an alkyl group, an alkenyl group, an alkynyl group, an aryl group, a cyano group, a hydroxy group, a carboxy group, an alkoxy group, an aryloxy group, a silyloxy group, an acyloxy group, a carbamoyloxy group, an alkoxycarbonyloxy group, an aryloxycarbonyloxy group, an amino group, an acylamino group, an aminocarbonylamino group, an alkoxycarbonylamino group, an aryloxycarbonylamino group, a sulfamoylamino group, an alkyl or aryl-sulfonyl amino group, a mercapto group, an alkylthio group, an arylthio group, a sulfamoyl group, a sulfo group, an alkyl- or aryl-sulfinyl group, an alkyl- or aryl-sulfonyl group, an acyl group, an aryloxycarbonyl group, an alkoxycarbonyl group, a carbamoyl group, an imido group, a phosphino group, a phosphinyl group, a phosphinyloxy group, a phosphinylamino group, or a silyl group, more preferably a hydrogen atom, a halogen atom, an alkyl group, an alkenyl group, an aryl group, a cyano group, a hydroxy group, a carboxy group, an alkoxy group, an aryloxy group, a silyloxy group, an amino group, an alkylthio group, an arylthio group, an imido group, or a silyl group, still more preferably, a hydrogen atom, a halogen atom, an alkyl group, an aryl group, an alkoxy group, an aryloxy group, a silyloxy group, or an amino group, most preferably a hydrogen atom, or an alkyl group.

In the invention, among respective combinations of $R^{111}$ and $R^{121}$, $R^{112}$ and $R^{122}$, $R^{113}$ and $R^{123}$, $R^{114}$ and $R^{124}$, $R^{115}$ and $R^{125}$, and $R^{116}$ and $R^{126}$, at least one combination is composed of groups that are different from each other. Thereby, a triarylamine derivative which is good in light resistance, wet heat resistance and solubility is obtained.

Further, $R^{111}$ and $R^{112}$ may be connected to each other to form a ring; $R^{111}$ and $R^{114}$ may be connected to each other to form a ring; $R^{113}$ and $R^{114}$ may be connected to each other to form a ring; $R^{113}$ and $R^{123}$ may be connected to each other to form a ring; $R^{123}$ and $R^{124}$ may be connected to each other to form a ring; $R^{121}$ and $R^{124}$ may be connected to each other to form a ring; $R^{121}$ and $R^{122}$ may be connected to each other to form a ring; and the two $R^{116}$s which are bound to different phenyl groups may be connected to each other to form a ring. By formation of the ring, light resistance, wet heat resistance and solubility may be further improved.

In addition, in the invention, it is preferable that at least one group selected from $R^{111}$, $R^{121}$, $R^{112}$ and $R^{122}$ is different from the remainder of these groups from the viewpoints of light resistance, wet heat resistance and solubility. Thereby, the maximum absorption wavelength of the triarylamine derivative according to the invention may be easily adjusted to a desired maximum absorption wavelength.

Furthermore, it is preferable that at least one group selected from $R^{113}$, $R^{114}$, $R^{115}$, $R^{116}$, $R^{123}$, $R^{124}$, $R^{125}$ and $R^{126}$ is different from the remainder of these groups from the viewpoints of light resistance, wet heat resistance and solubility. Thereby, the maximum absorption wavelength of the triarylamine derivative according to the invention may be easily adjusted to a desired maximum absorption wavelength.

In Formula (I), $X^{m-}$ represents a monovalent or divalent anion. Specific examples of $X^{m-}$ include a perchlorate ion, a hexafluoroantimonate ion, a hexafluorophosphate ion, a tetrafluoroborate ion, a nitrate ion, a sulfate ion, a p-toluenesulphonate ion (TsO⁻), a trifluoromethanesulfonate ion, and an anion represented by any of the following Formulae (II) to (IV).

In the invention, from the viewpoints of wet heat resistance and solubility, a perchlorate ion, a hexafluoroantimonate ion, a hexafluorophosphate ion, a tetrafluoroborate ion, or an anion represented by any of the following Formulae (II) to (IV) is preferable, and an anion represented by any of the following Formulae (II) to (IV) is more preferable.

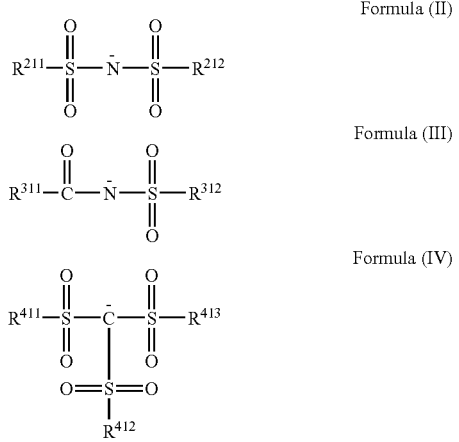

Formula (II)

Formula (III)

Formula (IV)

In Formulae (II) to (IV), $R^{211}$, $R^{212}$, $R^{311}$, $R^{312}$, $R^{411}$, $R^{412}$ and $R^{413}$ each independently represent an aliphatic group, an aromatic group or a heterocyclic group. The aliphatic group and the aromatic group are as described above. Examples of the heterocyclic group include the heterocyclic groups listed as examples of substituents on the alkyl moieties of a substituted alkyl group, a substituted alkenyl group, a substituted alkynyl group and a substituted aralkyl group. Thereby, an infrared absorbing triarylamine derivative having better wet heat resistance may be obtained.

In the invention, from the viewpoints of wet heat resistance and solubility, $R^{211}$, $R^{212}$, $R^{311}$, $R^{312}$, $R^{411}$, $R^{412}$ and $R^{413}$ each independently represent preferably an aliphatic group having a halogen atom, an aromatic group having a halogen atom, or a heterocyclic group having a halogen atom. It is more preferable that the halogen atom is a fluorine atom. Thereby, wet heat resistance and solubility are further improved.

$R^{211}$, $R^{212}$, $R^{311}$, $R^{312}$, $R^{411}$, $R^{412}$ and $R^{413}$ each independently represent preferably an alkyl group, an alkenyl group, an alkynyl group, an aryl group or a heterocyclic group, more preferably an alkyl group having a carbon number of from 1 to 20, an alkenyl group having a carbon number of from 2 to 20, an alkynyl group having a carbon number of from 2 to 20, or an aryl group having a carbon number of from 6 to 20, still more preferably an alkyl group having a carbon number of from 1 to 10, an alkenyl group having a carbon number of from 2 to 10, or an aryl group having a carbon number of from 6 to 10, further preferably an alkyl group having a carbon number of from 1 to 8 or an aryl group having a carbon number of from 6 to 8, most preferably an alkyl group having a carbon number of from 1 to 6. Among them, a perfluoroalkyl group represented by $C_nF_{2n+1}$ wherein n represents an integer of from 1 to 6 is desirable.

In the compound represented by Formula (I) in the invention, from the viewpoints of light resistance, wet heat resistance and solubility, it is preferable that $R^{111}$, $R^{112}$, $R^{121}$ and $R^{122}$ each independently represent a hydrogen atom, an alkyl group, or an aryl group, one or two groups selected from $R^{111}$, $R^{112}$, $R^{121}$ and $R^{122}$ are different from the remainder of these groups, $R^{211}$, $R^{212}$, $R^{311}$, $R^{312}$, $R^{411}$, $R^{412}$ and $R^{413}$ each independently represent a hydrogen atom, an alkyl group, an aryl group, or a substituent, and $X^{m-}$ represents a perchlorate ion, a hexafluoroantimonate ion, a hexafluorophosphate ion, a tetrafluoroborate ion, or an anion represented by any of Formulae (II) to (IV). It is also preferable that $R^{111}$, $R^{112}$, $R^{121}$ and $R^{122}$ each independently represent a hydrogen atom, an alkyl group, or an aryl group, $R^{211}$, $R^{212}$ $R^{311}$, $R^{312}$, $R^{411}$, $R^{412}$ and $R^{413}$ each independently represent a hydrogen atom, an alkyl group, an aryl group, or a substituent, one group selected from $R^{211}$, $R^{212}$, $R^{311}$, $R^{312}$, $R^{411}$, $R^{412}$ and $R^{413}$ is different from the remainder of these groups, and $X^{m-}$ represents a perchlorate ion, a hexafluoroantimonate ion, a hexafluorophosphate ion, a tetrafluoroborate ion, or an anion represented by any of Formulae (II) to (IV).

It is more preferable that $R^{111}$, $R^{112}$, $R^{121}$ and $R^{122}$ each independently represent an alkyl group, one or two groups selected from $R^{111}$, $R^{112}$, $R^{121}$ and $R^{122}$ are different from the remainder of these groups, $R^{211}$, $R^{212}$, $R^{311}$, $R^{312}$, $R^{411}$, $R^{412}$ and $R^{413}$ each independently represent a hydrogen atom, and $X^{m-}$ represents an anion represented by any one of Formulae (II) to (IV); it is also more preferable that $R^{111}$, $R^{112}$, $R^{121}$ and $R^{122}$ each independently represent an alkyl group, $R^{211}$, $R^{212}$, $R^{311}$, $R^{411}$, $R^{412}$ and $R^{413}$ each independently represent a hydrogen atom, an alkyl group, an aryl group, an alkoxy group, a cyano group, or an acyl group, one group selected from $R^{211}$, $R^{212}$, $R^{311}$, $R^{312}$, $R^{411}$, $R^{412}$ and $R^{413}$ is different from the remainder of these groups, and $X^{m-}$ represents an anion represented by any of Formulae (II) to (IV).

As a specific example of the triarylamine derivative (diimmonium compound) represented by Formula (I) according to the invention, compounds 1 to 249 are illustrated below, but the invention is not limited to them.

Specific examples of the diimmonium compound in which $X^{m-}$ in the compound represented by Formula (I) is a metal salt of an inorganic acid (compound 1 to compound 50, compound 206 to compound 213) are illustrated in the following Table 1, Table 2 and separate chemical formulae, specific examples of the diimmonium compound in which $X^{m-}$ in the compound represented by Formula (I) is represented by Formula (II) (compound 51 to compound 100, compound 214 to compound 225) are illustrated in the following Table 3, Table 4 and separate chemical formulae, specific examples of the diimmonium compound in which $X^{m-}$ is represented by Formula (III) (compound 101 to compound 150, compound 226 to compound 237) are illustrated in the following Table 5, Table 6 and separate chemical formulae, and specific examples of the diimmonium compound in which $X^{m-}$ is represented by Formula (IV) (compound 151 to compound 205, compound 238 to compound 249) are illustrated in the following Table 7, Table 8 and separate chemical formulae, respectively.

TABLE 1

| No. | $(R^{111}, R^{112})$, $(R^{121}, R^{122})$ | $(R^{113}, R^{114}, R^{115}, R^{116})$, $(R^{123}, R^{124}, R^{125}, R^{126})$ | $(X^{m-})_n$ |
|---|---|---|---|
| 1 | $(CH_3, CH_3)$, $(CH_3, C_2H_5)$ | 2(H, H, H, H) | $(SbF_6^-)_2$ |
| 2 | $(C_2H_5, C_2H_5)$, $(CH_3, C_2H_5)$ | 2(H, H, H, H) | $(SbF_6^-)_2$ |
| 3 | $(n-C_3H_7, n-C_3H_7)$, $(CH_3, C_2H_5)$ | 2(H, H, H, H) | $(SbF_6^-)_2$ |
| 4 | $(iso-C_3H_7, iso-C_3H_7)$, $(CH_3, C_2H_5)$ | 2(H, H, H, H) | $(SbF_6^-)_2$ |
| 5 | $(n-C_4H_9, n-C_4H_9)$, $(CH_3, C_2H_5)$ | 2(H, H, H, H) | $(SbF_6^-)_2$ |
| 6 | $(n-C_4H_9, n-C_4H_9,)$, $(C_2H_5, C_2H_5)$ | 2(H, H, H, H) | $(SbF_6^-)_2$ |
| 7 | $(iso-C_4H_9, iso-C_4H_9)$, $(C_2H_5, C_2H_5)$ | 2(H, H, H, H) | $(SbF_6^-)_2$ |
| 8 | $(sec-C_4H_9, sec-C_4H_9)$, $(CH_3, C_2H_5)$ | 2(H, H, H, H) | $(SbF_6^-)_2$ |
| 9 | $(tert-C_4H_9, tert-C_4H_9)$, $(CH_3, C_2H_5)$ | 2(H, H, H, H) | $(SbF_6^-)_2$ |
| 10 | $(n-C_5H_{11}, n-C_5H_{11})$, $(CH_3, C_2H_5)$ | 2(H, H, H, H) | $(SbF_6^-)_2$ |
| 11 | $(iso-C_5H_{11}, iso-C_5H_{11})$, $(CH_3, C_2H_5)$ | 2(H, H, H, H) | $(SbF_6^-)_2$ |
| 12 | $(n-C_6H_{13}, n-C_6H_{13})$, $(CH_3, C_2H_5)$ | 2(H, H, H, H) | $(SbF_6^-)_2$ |
| 13 | $(cyclo-C_6H_{11}, cyclo-C_6H_{11})$, $(CH_3, C_2H_5)$ | 2(H, H, H, H) | $(SbF_6^-)_2$ |
| 14 | $(C_2H_4CN, C_2H_4CN)$, $(CH_3, C_2H_5)$ | 2(H, H, H, H) | $(SbF_6^-)_2$ |
| 15 | $(C_3H_6CN, C_3H_6CN)$, $(CH_3, C_2H_5)$ | 2(H, H, H, H) | $(SbF_6^-)_2$ |
| 16 | $(C_3H_6NO_2, C_3H_6NO_2)$, $(CH_3, C_2H_5)$ | 2(H, H, H, H) | $(SbF_6^-)_2$ |
| 17 | $(C_3H_6OH, C_3H_6OH)$, $(CH_3, C_2H_5)$ | 2(H, H, H, H) | $(SbF_6^-)_2$ |
| 18 | $(CH_2CCl_3, CH_2CCl_3)$, $(CH_3, C_2H_5)$ | 2(H, H, H, H) | $(SbF_6^-)_2$ |
| 19 | $(CF_3, CF_3)$, $(CH_3, C_2H_5)$ | 2(H, H, H, H) | $(SbF_6^-)_2$ |
| 20 | $(C_2F_5, C_2F_5)$, $(CH_3, C_2H_5)$ | 2(H, H, H, H) | $(SbF_6^-)_2$ |
| 21 | $(CF_2CF_2CF_3, CF_2CF_2CF_3)$, $(CH_3, C_2H_5)$ | 2(H, H, H, H) | $(SbF_6^-)_2$ |
| 22 | $(CH_2CH_2CF_3, CH_2CH_2CF_3)$, $(CH_3, C_2H_5)$ | 2(H, H, H, H) | $(SbF_6^-)_2$ |
| 23 | $(CH_2CH_2OCH_3, CH_2CH_2OCH_3)$, $(CH_3, C_2H_5)$ | 2(H, H, H, H) | $(SbF_6^-)_2$ |
| 24 | $(CH_2CH_2COOH_3, CH_2CH_2COOH_3)$, $(CH_3, C_2H_5)$ | 2(H, H, H, H) | $(SbF_6^-)_2$ |
| 25 | (H, H), $(CH_3, C_2H_5)$ | 2(H, H, H, H) | $(SbF_6^-)_2$ |
| 26 | (Ph, Ph), $(CH_3, C_2H_5)$ | 2(H, H, H, H) | $(SbF_6^-)_2$ |

TABLE 2

| No. | $(R^{111}, R^{112})$, $(R^{121}, R^{122})$ | $(R^{113}, R^{114}, R^{115}, R^{116})$, $(R^{123}, R^{124}, R^{125}, R^{126})$ | $(X^{m-})_n$ |
|---|---|---|---|
| 27 | $2(iso-C_4H_9, iso-C_4H_9)$ | $(CH_3, H, H, H)$, (H, H, H, H) | $(SbF_6^-)_2$ |
| 28 | $2(n-C_4H_9, n-C_4H_9)$ | $(CH_3, H, H, H)$, (H, H, H, H) | $(SbF_6^-)_2$ |
| 29 | $2(n-C_4H_9, n-C_4H_9)$ | $(H, CH_3, H, H)$, (H, H, H, H) | $(SbF_6^-)_2$ |
| 30 | $2(n-C_4H_9, n-C_4H_9)$ | $(C_2H_5, H, H, H)$, (H, H, H, H) | $(SbF_6^-)_2$ |
| 31 | $2(n-C_4H_9, n-C_4H_9)$ | $(H, C_2H_5, H, H)$, (H, H, H, H) | $(SbF_6^-)_2$ |
| 32 | $2(n-C_4H_9, n-C_4H_9)$ | $(OCH_3, H, H, H)$, (H, H, H, H) | $(SbF_6^-)_2$ |
| 33 | $2(n-C_4H_9, n-C_4H_9)$ | $(H, OCH_3, H, H)$, (H, H, H, H) | $(SbF_6^-)_2$ |
| 34 | $2(n-C_4H_9, n-C_4H_9)$ | (Cl, H, H, H), (H, H, H, H) | $(SbF_6^-)_2$ |
| 35 | $2(n-C_4H_9, n-C_4H_9)$ | (H, Cl, H, H), (H, H, H, H) | $(SbF_6^-)_2$ |
| 36 | $2(n-C_4H_9, n-C_4H_9)$ | (F, H, H, H), (H, H, H, H) | $(SbF_6^-)_2$ |
| 37 | $2(n-C_4H_9, n-C_4H_9)$ | (H, F, H, H), (H, H, H, H) | $(SbF_6^-)_2$ |
| 38 | $2(n-C_4H_9, n-C_4H_9)$ | (Ph, H, H, H), (H, H, H, H) | $(SbF_6^-)_2$ |
| 39 | $2(n-C_4H_9, n-C_4H_9)$ | (H, Ph, H, H), (H, H, H, H) | $(SbF_6^-)_2$ |
| 40 | $2(n-C_4H_9, n-C_4H_9)$ | (Ac, H, H, H), (H, H, H, H) | $(SbF_6^-)_2$ |
| 41 | $2(n-C_4H_9, n-C_4H_9)$ | (H, Ac, H, H), (H, H, H, H) | $(SbF_6^-)_2$ |
| 42 | $2(n-C_4H_9, n-C_4H_9)$ | (CN, H, H, H), (H, H, H, H) | $(SbF_6^-)_2$ |
| 43 | $2(n-C_4H_9, n-C_4H_9)$ | (H, CN, H, H), (H, H, H, H) | $(SbF_6^-)_2$ |
| 44 | $2(n-C_4H_9, n-C_4H_9)$ | $(CH_3, H, H, H)$, (H, H, H, H) | $(ClO_4^-)_2$ |
| 45 | $2(n-C_4H_9, n-C_4H_9)$ | $(CH_3, H, H, H)$, (H, H, H, H) | $(PF_6^-)_2$ |
| 46 | $2(n-C_4H_9, n-C_4H_9)$ | $(CH_3, H, H, H)$, (H, H, H, H) | $(NO_3^-)_2$ |
| 47 | $2(n-C_4H_9, n-C_4H_9)$ | $(CH_3, H, H, H)$, (H, H, H, H) | $(TsO^-)_2$ |
| 48 | $2(n-C_4H_9, n-C_4H_9)$ | $(CH_3, H, H, H)$, (H, H, H, H) | $(CF_3SO_3^-)_2$ |
| 49 | $2(n-C_4H_9, n-C_4H_9)$ | $(CH_3, H, H, H)$, (H, H, H, H) | $(BF_4^-)_2$ |
| 50 | $2(n-C_4H_9, n-C_4H_9)$ | $(CH_3, H, H, H)$, (H, H, H, H) | $(SO_4^{2-})$ |

TABLE 3

| No. | $(R^{111}, R^{112})$, $(R^{121}, R^{122})$ | $(R^{113}, R^{114}, R^{115}, R^{116})$, $(R^{123}, R^{124}, R^{125}, R^{126})$ | $(R^{211}, R^{212})$ |
|---|---|---|---|
| 51 | $(CH_3, CH_3)$, $(CH_3, C_2H_5)$ | 2(H, H, H, H) | $(CF_3, CF_3)$ |
| 52 | $(C_2H_5, C_2H_5)$, $(CH_3, C_2H_5)$ | 2(H, H, H, H) | $(CF_3, CF_3)$ |
| 53 | $(n-C_3H_7, n-C_3H_7)$, $(CH_3, C_2H_5)$ | 2(H, H, H, H) | $(CF_3, CF_3)$ |
| 54 | $(iso-C_3H_7, iso-C_3H_7)$, $(CH_3, C_2H_5)$ | 2(H, H, H, H) | $(CF_3, CF_3)$ |
| 55 | $(n-C_4H_9, n-C_4H_9,)$, $(CH_3, C_2H_5)$ | 2(H, H, H, H) | $(CF_3, CF_3)$ |
| 56 | $(n-C_4H_9, n-C_4H_9,)$, $(C_2H_5, C_2H_5)$ | 2(H, H, H, H) | $(CF_3, CF_3)$ |
| 57 | $(iso-C_4H_9, iso-C_4H_9)$, $(C_2H_5, C_2H_5)$ | 2(H, H, H, H) | $(CF_3, CF_3)$ |
| 58 | $(sec-C_4H_9, sec-C_4H_9)$, $(CH_3, C_2H_5)$ | 2(H, H, H, H) | $(CF_3, CF_3)$ |
| 59 | $(tert-C_4H_9, tert-C_4H_9)$, $(CH_3, C_2H_5)$ | 2(H, H, H, H) | $(CF_3, CF_3)$ |

TABLE 3-continued

| No. | $(R^{111}, R^{112})$, $(R^{121}, R^{122})$ | $(R^{113}, R^{114}, R^{115}, R^{116})$, $(R^{123}, R^{124}, R^{125}, R^{126})$ | $(R^{211}, R^{212})$ |
|---|---|---|---|
| 60 | (n-$C_5H_{11}$, n-$C_5H_{11}$), ($CH_3$, $C_2H_5$) | 2(H, H, H, H) | ($CF_3$, $CF_3$) |
| 61 | (iso-$C_5H_{11}$, iso-$C_5H_{11}$), ($CH_3$, $C_2H_5$) | 2(H, H, H, H) | ($CF_3$, $CF_3$) |
| 62 | (n-$C_6H_{13}$, n-$C_6H_{13}$), ($CH_3$, $C_2H_5$) | 2(H, H, H, H) | ($CF_3$, $CF_3$) |
| 63 | (cyclo-$C_6H_{11}$, cyclo-$C_6H_{11}$), ($CH_3$, $C_2H_5$) | 2(H, H, H, H) | ($CF_3$, $CF_3$) |
| 64 | ($C_2H_4CN$, $C_2H_4CN$), ($CH_3$, $C_2H_5$) | 2(H, H, H, H) | ($CF_3$, $CF_3$) |
| 65 | ($C_3H_6CN$, $C_3H_6CN$), ($CH_3$, $C_2H_5$) | 2(H, H, H, H) | ($CF_3$, $CF_3$) |
| 66 | ($C_3H_6NO_2$, $C_3H_6NO_2$), ($CH_3$, $C_2H_5$) | 2(H, H, H, H) | ($CF_3$, $CF_3$) |
| 67 | ($C_3H_6OH$, $C_3H_6OH$), ($CH_3$, $C_2H_5$) | 2(H, H, H, H) | ($CF_3$, $CF_3$) |
| 68 | ($CH_2CCl_3$, $CH_2CCl_3$), ($CH_3$, $C_2H_5$) | 2(H, H, H, H) | ($CF_3$, $CF_3$) |
| 69 | ($CF_3$, $CF_3$), ($CH_3$, $C_2H_5$) | 2(H, H, H, H) | ($CF_3$, $CF_3$) |
| 70 | ($C_2F_5$, $C_2F_5$), ($CH_3$, $C_2H_5$) | 2(H, H, H, H) | ($CF_3$, $CF_3$) |
| 71 | ($CF_2CF_2CF_3$, $CF_2CF_2CF_3$), ($CH_3$, $C_2H_5$) | 2(H, H, H, H) | ($CF_3$, $CF_3$) |
| 72 | ($CH_2CH_2CF_3$, $CH_2CH_2CF_3$), ($CH_3$, $C_2H_5$) | 2(H, H, H, H) | ($CF_3$, $CF_3$) |
| 73 | ($CH_2CH_2OCH_3$, $CH_2CH_2OCH_3$), ($CH_3$, $C_2H_5$) | 2(H, H, H, H) | ($CF_3$, $CF_3$) |
| 74 | ($CH_2CH_2COOH$, $CH_2CH_2COOH_3$), ($CH_3$, $C_2H_5$) | 2(H, H, H, H) | ($CF_3$, $CF_3$) |
| 75 | (H, H), ($CH_3$, $C_2H_5$) | 2(H, H, H, H) | ($CF_3$, $CF_3$) |
| 76 | (Ph, Ph), ($CH_3$, $C_2H_5$) | 2(H, H, H, H) | ($CF_3$, $CF_3$) |

TABLE 4

| No. | $(R^{111}, R^{112})$, $(R^{121}, R^{122})$ | $(R^{113}, R^{114}, R^{115}, R^{116})$, $(R^{123}, R^{124}, R^{125}, R^{126})$ | $(R^{211}, R^{212})$ |
|---|---|---|---|
| 77 | 2(iso-$C_4H_9$, iso-$C_4H_9$) | ($CH_3$, H, H, H), (H, H, H, H) | ($CF_3$, $CF_3$) |
| 78 | 2(iso-$C_4H_9$, iso-$C_4H_9$) | (H, $CH_3$, H, H), (H, H, H, H) | ($CF_3$, $CF_3$) |
| 79 | 2(n-$C_4H_9$, n-$C_4H_9$) | ($CH_3$, H, H, H), (H, H, H, H) | ($CF_3$, $CF_3$) |
| 80 | 2(n-$C_4H_9$, n-$C_4H_9$) | (H, $CH_3$, H, H), (H, H, H, H) | ($CF_3$, $CF_3$) |
| 81 | 2(n-$C_4H_9$, n-$C_4H_9$) | ($C_2H_5$, H, H, H), (H, H, H, H) | ($CF_3$, $CF_3$) |
| 82 | 2(n-$C_4H_9$, n-$C_4H_9$) | (H, $C_2H_5$, H, H), (H, H, H, H) | ($CF_3$, $CF_3$) |
| 83 | 2(n-$C_4H_9$, n-$C_4H_9$) | ($OCH_3$, H, H, H), (H, H, H, H) | ($CF_3$, $CF_3$) |
| 84 | 2(n-$C_4H_9$, n-$C_4H_9$) | (H, $OCH_3$, H, H), (H, H, H, H) | ($CF_3$, $CF_3$) |
| 85 | 2(n-$C_4H_9$, n-$C_4H_9$) | (Cl, H, H, H), (H, H, H, H) | ($CF_3$, $CF_3$) |
| 86 | 2(n-$C_4H_9$, n-$C_4H_9$) | (H, Cl, H, H), (H, H, H, H) | ($CF_3$, $CF_3$) |
| 87 | 2(n-$C_4H_9$, n-$C_4H_9$) | (F, H, H, H), (H, H, H, H) | ($CF_3$, $CF_3$) |
| 88 | 2(n-$C_4H_9$, n-$C_4H_9$) | (H, F, H, H), (H, H, H, H) | ($CF_3$, $CF_3$) |
| 89 | 2(n-$C_4H_9$, n-$C_4H_9$) | (Ph, H, H, H), (H, H, H, H) | ($CF_3$, $CF_3$) |
| 90 | 2(n-$C_4H_9$, n-$C_4H_9$) | (H, Ph, H, H), (H, H, H, H) | ($CF_3$, $CF_3$) |
| 91 | 2(n-$C_4H_9$, n-$C_4H_9$) | (Ac, H, H, H), (H, H, H, H) | ($CF_3$, $CF_3$) |
| 92 | 2(n-$C_4H_9$, n-$C_4H_9$) | (H, Ac, H, H), (H, H, H, H) | ($CF_3$, $CF_3$) |
| 93 | 2(n-$C_4H_9$, n-$C_4H_9$) | (CN, H, H, H), (H, H, H, H) | ($CF_3$, $CF_3$) |
| 94 | 2(n-$C_4H_9$, n-$C_4H_9$) | (H, CN, H, H), (H, H, H, H) | ($CF_3$, $CF_3$) |
| 95 | 2(n-$C_4H_9$, n-$C_4H_9$) | ($CH_3$, H, H, H), (H, H, H, H) | ($CH_3$, $CH_3$) |
| 96 | 2(n-$C_4H_9$, n-$C_4H_9$) | ($CH_3$, H, H, H), (H, H, H, H) | ($C_2F_5$, $C_2F_5$) |
| 97 | 2(n-$C_4H_9$, n-$C_4H_9$) | ($CH_3$, H, H, H), (H, H, H, H) | ($CH_3$, $C_6H_4CH_3$) |
| 98 | 2(n-$C_4H_9$, n-$C_4H_9$) | ($CH_3$, H, H, H), (H, H, H, H) | ($CF_3$, $CH_3$) |
| 99 | 2(n-$C_4H_9$, n-$C_4H_9$) | ($CH_3$, H, H, H), (H, H, H, H) | ($CF_3$, n-$C_4F_9$) |
| 100 | 2(n-$C_4H_9$, n-$C_4H_9$) | ($CH_3$, H, H, H), (H, H, H, H) | ($CF_3$, $C_6F_5$) |

TABLE 5

| No. | $(R^{111}, R^{112})$, $(R^{121}, R^{122})$ | $(R^{113}, R^{114}, R^{115}, R^{116})$, $(R^{123}, R^{124}, R^{125}, R^{126})$ | $(R^{211}, R^{212})$ |
|---|---|---|---|
| 101 | ($CH_3$, $CH_3$), ($CH_3$, $C_2H_5$) | 2(H, H, H, H) | ($CF_3$, $CF_3$) |
| 102 | ($C_2H_5$, $C_2H_5$), ($CH_3$, $C_2H_5$) | 2(H, H, H, H) | ($CF_3$, $CF_3$) |
| 103 | (n-$C_3H_7$, n-$C_3H_7$), ($CH_3$, $C_2H_5$) | 2(H, H, H, H) | ($CF_3$, $CF_3$) |
| 104 | (iso-$C_3H_7$, iso-$C_3H_7$), ($CH_3$, $C_2H_5$) | 2(H, H, H, H) | ($CF_3$, $CF_3$) |
| 105 | (n-$C_4H_9$, n-$C_4H_9$), ($CH_3$, $C_2H_5$) | 2(H, H, H, H) | ($CF_3$, $CF_3$) |
| 106 | (n-$C_4H_9$, n-$C_4H_9$), ($C_2H_5$, $C_2H_5$) | 2(H, H, H, H) | ($CF_3$, $CF_3$) |
| 107 | (iso-$C_4H_9$, iso-$C_4H_9$), ($C_2H_5$, $C_2H_5$) | 2(H, H, H, H) | ($CF_3$, $CF_3$) |
| 108 | (sec-$C_4H_9$, sec-$C_4H_9$), ($CH_3$, $C_2H_5$) | 2(H, H, H, H) | ($CF_3$, $CF_3$) |
| 109 | (tert-$C_4H_9$, tert-$C_4H_9$), ($CH_3$, $C_2H_5$) | 2(H, H, H, H) | ($CF_3$, $CF_3$) |
| 110 | (n-$C_5H_{11}$, n-$C_5H_{11}$), ($CH_3$, $C_2H_5$) | 2(H, H, H, H) | ($CF_3$, $CF_3$) |
| 111 | (iso-$C_5H_{11}$, iso-$C_5H_{11}$), ($CH_3$, $C_2H_5$) | 2(H, H, H, H) | ($CF_3$, $CF_3$) |
| 112 | (n-$C_6H_{13}$, n-$C_6H_{13}$), ($CH_3$, $C_2H_5$) | 2(H, H, H, H) | ($CF_3$, $CF_3$) |
| 113 | (cyclo-$C_6H_{11}$, cyclo-$C_6H_{11}$), ($CH_3$, $C_2H_5$) | 2(H, H, H, H) | ($CF_3$, $CF_3$) |
| 114 | ($C_2H_4CN$, $C_2H_4CN$), ($CH_3$, $C_2H_5$) | 2(H, H, H, H) | ($CF_3$, $CF_3$) |
| 115 | ($C_3H_6CN$, $C_3H_6CN$), ($CH_3$, $C_2H_5$) | 2(H, H, H, H) | ($CF_3$, $CF_3$) |
| 116 | ($C_3H_6NO_2$, $C_3H_6NO_2$), ($CH_3$, $C_2H_5$) | 2(H, H, H, H) | ($CF_3$, $CF_3$) |
| 117 | ($C_3H_6OH$, $C_3H_6OH$), ($CH_3$, $C_2H_5$) | 2(H, H, H, H) | ($CF_3$, $CF_3$) |
| 118 | ($CH_2CCl_3$, $CH_2CCl_3$), ($CH_3$, $C_2H_5$) | 2(H, H, H, H) | ($CF_3$, $CF_3$) |

TABLE 5-continued

| No. | $(R^{111}, R^{112})$, $(R^{121}, R^{122})$ | $(R^{113}, R^{114}, R^{115}, R^{116})$, $(R^{123}, R^{124}, R^{125}, R^{126})$ | $(R^{211}, R^{212})$ |
|---|---|---|---|
| 119 | $(CF_3, CF_3)$, $(CH_3, C_2H_5)$ | 2(H, H, H, H) | $(CF_3, CF_3)$ |
| 120 | $(C_2F_5, C_2F_5)$, $(CH_3, C_2H_5)$ | 2(H, H, H, H) | $(CF_3, CF_3)$ |
| 121 | $(CF_2CF_2CF_3, CF_2CF_2CF_3)$, $(CH_3, C_2H_5)$ | 2(H, H, H, H) | $(CF_3, CF_3)$ |
| 122 | $(CH_2CH_2CF_3, CH_2CH_2CF_3)$, $(CH_3, C_2H_5)$ | 2(H, H, H, H) | $(CF_3, CF_3)$ |
| 123 | $(CH_2CH_2OCH_3, CH_2CH_2OCH_3)$, $(CH_3, C_2H_5)$ | 2(H, H, H, H) | $(CF_3, CF_3)$ |
| 124 | $(CH_2CH_2COOH, CH_2CH_2COOH)$, $(CH_3, C_2H_5)$ | 2(H, H, H, H) | $(CF_3, CF_3)$ |
| 125 | (H, H), $(CH_3, C_2H_5)$ | 2(H, H, H, H) | $(CF_3, CF_3)$ |
| 126 | (Ph, Ph), $(CH_3, C_2H_5)$ | 2(H, H, H, H) | $(CF_3, CF_3)$ |

TABLE 6

| No. | $(R^{111}, R^{112})$, $(R^{121}, R^{122})$ | $(R^{113}, R^{114}, R^{115}, R^{116})$, $(R^{123}, R^{124}, R^{125}, R^{126})$ | $(R^{311}, R^{312})$ |
|---|---|---|---|
| 127 | 2(iso-$C_4H_9$, iso-$C_4H_9$) | $(CH_3, H, H, H)$, (H, H, H, H) | $(CF_3, CF_3)$ |
| 128 | 2(iso-$C_4H_9$, iso-$C_4H_9$) | $(H, CH_3, H, H)$, (H, H, H, H) | $(CF_3, CF_3)$ |
| 129 | 2(n-$C_4H_9$, n-$C_4H_9$) | $(CH_3, H, H, H)$, (H, H, H, H) | $(CF_3, CF_3)$ |
| 130 | 2(n-$C_4H_9$, n-$C_4H_9$) | $(H, CH_3, H, H)$, (H, H, H, H) | $(CF_3, CF_3)$ |
| 131 | 2(n-$C_4H_9$, n-$C_4H_9$) | $(C_2H_5, H, H, H)$, (H, H, H, H) | $(CF_3, CF_3)$ |
| 132 | 2(n-$C_4H_9$, n-$C_4H_9$) | $(H, C_2H_5, H, H)$, (H, H, H, H) | $(CF_3, CF_3)$ |
| 133 | 2(n-$C_4H_9$, n-$C_4H_9$) | $(OCH_3, H, H, H)$, (H, H, H, H) | $(CF_3, CF_3)$ |
| 134 | 2(n-$C_4H_9$, n-$C_4H_9$) | $(H, OCH_3, H, H)$, (H, H, H, H) | $(CF_3, CF_3)$ |
| 135 | 2(n-$C_4H_9$, n-$C_4H_9$) | (Cl, H, H, H), (H, H, H, H) | $(CF_3, CF_3)$ |
| 136 | 2(n-$C_4H_9$, n-$C_4H_9$) | (H, Cl, H, H), (H, H, H, H) | $(CF_3, CF_3)$ |
| 137 | 2(n-$C_4H_9$, n-$C_4H_9$) | (F, H, H, H), (H, H, H, H) | $(CF_3, CF_3)$ |
| 138 | 2(n-$C_4H_9$, n-$C_4H_9$) | (H, F, H, H), (H, H, H, H) | $(CF_3, CF_3)$ |
| 139 | 2(n-$C_4H_9$, n-$C_4H_9$) | (Ph, H, H, H), (H, H, H, H) | $(CF_3, CF_3)$ |
| 140 | 2(n-$C_4H_9$, n-$C_4H_9$) | (H, Ph, H, H), (H, H, H, H) | $(CF_3, CF_3)$ |
| 141 | 2(n-$C_4H_9$, n-$C_4H_9$) | (Ac, H, H, H), (H, H, H, H) | $(CF_3, CF_3)$ |
| 142 | 2(n-$C_4H_9$, n-$C_4H_9$) | (H, Ac, H, H), (H, H, H, H) | $(CF_3, CF_3)$ |
| 143 | 2(n-$C_4H_9$, n-$C_4H_9$) | (CN, H, H, H), (H, H, H, H) | $(CF_3, CF_3)$ |
| 144 | 2(n-$C_4H_9$, n-$C_4H_9$) | (H, CN, H, H), (H, H, H, H) | $(CF_3, CF_3)$ |
| 145 | 2(n-$C_4H_9$, n-$C_4H_9$) | $(CH_3, H, H, H)$, (H, H, H, H) | $(CH_3, CH_3)$ |
| 146 | 2(n-$C_4H_9$, n-$C_4H_9$) | $(CH_3, H, H, H)$, (H, H, H, H) | $(C_2F_5, C_2F_5)$ |
| 147 | 2(n-$C_4H_9$, n-$C_4H_9$) | $(CH_3, H, H, H)$, (H, H, H, H) | $(CH_3, C_6H_4CH_3)$ |
| 148 | 2(n-$C_4H_9$, n-$C_4H_9$) | $(CH_3, H, H, H)$, (H, H, H, H) | $(CF_3, CH_3)$ |
| 149 | 2(n-$C_4H_9$, n-$C_4H_9$) | $(CH_3, H, H, H)$, (H, H, H, H) | $(CF_3, n-C_4F_9)$ |
| 150 | 2(n-$C_4H_9$, n-$C_4H_9$) | $(CH_3, H, H, H)$, (H, H, H, H) | $(CF_3, C_6F_5)$ |

TABLE 7

| No. | $(R^{111}, R^{112})$, $(R^{121}, R^{122})$ | $(R^{113}, R^{114}, R^{115}, R^{116})$, $(R^{123}, R^{124}, R^{125}, R^{126})$ | $(R^{411}, R^{412}, R^{413})$ |
|---|---|---|---|
| 151 | $(CH_3, CH_3)$, $(CH_3, C_2H_5)$ | 2(H, H, H, H) | $(CF_3, CF_3, CF_3)$ |
| 152 | $(C_2H_5, C_2H_5)$, $(CH_3, C_2H_5)$ | 2(H, H, H, H) | $(CF_3, CF_3, CF_3)$ |
| 153 | (n-$C_3H_7$, n-$C_3H_7$), $(CH_3, C_2H_5)$ | 2(H, H, H, H) | $(CF_3, CF_3, CF_3)$ |
| 154 | (iso-$C_3H_7$, iso-$C_3H_7$), $(CH_3, C_2H_5)$ | 2(H, H, H, H) | $(CF_3, CF_3, CF_3)$ |
| 155 | (n-$C_4H_9$, n-$C_4H_9$), $(CH_3, C_2H_5)$ | 2(H, H, H, H) | $(CF_3, CF_3, CF_3)$ |
| 156 | (n-$C_4H_9$, n-$C_4H_9$), $(C_2H_5, C_2H_5)$ | 2(H, H, H, H) | $(CF_3, CF_3, CF_3)$ |
| 157 | (iso-$C_4H_9$, iso-$C_4H_9$), $(C_2H_5, C_2H_5)$ | 2(H, H, H, H) | $(CF_3, CF_3, CF_3)$ |
| 158 | (sec-$C_4H_9$, sec-$C_4H_9$), $(CH_3, C_2H_5)$ | 2(H, H, H, H) | $(CF_3, CF_3, CF_3)$ |
| 159 | (tert-$C_4H_9$, tert-$C_4H_9$), $(CH_3, C_2H_5)$ | 2(H, H, H, H) | $(CF_3, CF_3, CF_3)$ |
| 160 | (n-$C_5H_{11}$, n-$C_5H_{11}$), $(CH_3, C_2H_5)$ | 2(H, H, H, H) | $(CF_3, CF_3, CF_3)$ |
| 161 | (iso-$C_5H_{11}$, iso-$C_5H_{11}$), $(CH_3, C_2H_5)$ | 2(H, H, H, H) | $(CF_3, CF_3, CF_3)$ |
| 162 | (n-$C_6H_{13}$, n-$C_6H_{13}$), $(CH_3, C_2H_5)$ | 2(H, H, H, H) | $(CF_3, CF_3, CF_3)$ |
| 163 | (cyclo-$C_6H_{11}$, cyclo-$C_6H_{11}$), $(CH_3, C_2H_5)$ | 2(H, H, H, H) | $(CF_3, CF_3, CF_3)$ |
| 164 | $(C_2H_4CN, C_2H_4CN)$, $(CH_3, C_2H_5)$ | 2(H, H, H, H) | $(CF_3, CF_3, CF_3)$ |
| 165 | $(C_3H_6CN, C_3H_6CN)$, $(CH_3, C_2H_5)$ | 2(H, H, H, H) | $(CF_3, CF_3, CF_3)$ |
| 166 | $(C_3H_6NO_2, C_3H_6NO_2)$, $(CH_3, C_2H_5)$ | 2(H, H, H, H) | $(CF_3, CF_3, CF_3)$ |
| 167 | $(C_3H_6OH, C_3H_6OH)$, $(CH_3, C_2H_5)$ | 2(H, H, H, H) | $(CF_3, CF_3, CF_3)$ |
| 168 | $(CH_2CCl_3, CH_2CCl_3)$, $(CH_3, C_2H_5)$ | 2(H, H, H, H) | $(CF_3, CF_3, CF_3)$ |
| 169 | $(CF_3, CF_3)$, $(CH_3, C_2H_5)$ | 2(H, H, H, H) | $(CF_3, CF_3, CF_3)$ |
| 170 | $(C_2F_5, C_2F_5)$, $(CH_3, C_2H_5)$ | 2(H, H, H, H) | $(CF_3, CF_3, CF_3)$ |
| 171 | $(CF_2CF_2CF_3, CF_2CF_2CF_3)$, $(CH_3, C_2H_5)$ | 2(H, H, H, H) | $(CF_3, CF_3, CF_3)$ |
| 172 | $(CH_2CH_2CF_3, CH_2CH_2CF_3)$, $(CH_3, C_2H_5)$ | 2(H, H, H, H) | $(CF_3, CF_3, CF_3)$ |
| 173 | $(CH_2CH_2OCH_3, CH_2CH_2OCH_3)$, $(CH_3, C_2H_5)$ | 2(H, H, H, H) | $(CF_3, CF_3, CF_3)$ |
| 174 | $(CH_2CH_2COOH, CH_2CH_2COOH)$, $(CH_3, C_2H_5)$ | 2(H, H, H, H) | $(CF_3, CF_3, CF_3)$ |
| 175 | (H, H), $(CH_3, C_2H_5)$ | 2(H, H, H, H) | $(CF_3, CF_3, CF_3)$ |
| 176 | (Ph, Ph), $(CH_3, CH_2H_5)$ | 2(H, H, H, H) | $(CF_3, CF_3, CF_3)$ |

TABLE 8

| No. | $(R^{111}, R^{112}), (R^{121}, R^{122})$ | $(R^{113}, R^{114}, R^{115}, R^{116}), (R^{123}, R^{124}, R^{125}, R^{126})$ | $(R^{411}, R^{412}, R^{413})$ |
|---|---|---|---|
| 177 | 2(iso-$C_4H_9$, iso-$C_4H_9$) | ($CH_3$, H, H, H), (H, H, H, H) | ($CF_3$, $CF_3$, $CF_3$) |
| 178 | 2(iso-$C_4H_9$, iso-$C_4H_9$) | (H, $CH_3$, H, H), (H, H, H, H) | ($CF_3$, $CF_3$, $CF_3$) |
| 179 | 2(n-$C_4H_9$, n-$C_4H_9$) | ($CH_3$, H, H, H), (H, H, H, H) | ($CF_3$, $CF_3$, $CF_3$) |
| 180 | 2(n-$C_4H_9$, n-$C_4H_9$) | (H, $CH_3$, H, H), (H, H, H, H) | ($CF_3$, $CF_3$, $CF_3$) |
| 181 | 2(n-$C_4H_9$, n-$C_4H_9$) | ($C_2H_5$, H, H, H), (H, H, H, H) | ($CF_3$, $CF_3$, $CF_3$) |
| 182 | 2(n-$C_4H_9$, n-$C_4H_9$) | (H, $C_2H_5$, H, H), (H, H, H, H) | ($CF_3$, $CF_3$, $CF_3$) |
| 183 | 2(n-$C_4H_9$, n-$C_4H_9$) | ($OCH_3$, H, H, H), (H, H, H, H) | ($CF_3$, $CF_3$, $CF_3$) |
| 184 | 2(n-$C_4H_9$, n-$C_4H_9$) | (H, $OCH_3$, H, H), (H, H, H, H) | ($CF_3$, $CF_3$, $CF_3$) |
| 185 | 2(n-$C_4H_9$, n-$C_4H_9$) | (Cl, H, H, H), (H, H, H, H) | ($CF_3$, $CF_3$, $CF_3$) |
| 186 | 2(n-$C_4H_9$, n-$C_4H_9$) | (H, Cl, H, H), (H, H, H, H) | ($CF_3$, $CF_3$, $CF_3$) |
| 187 | 2(n-$C_4H_9$, n-$C_4H_9$) | (F, H, H, H), (H, H, H, H) | ($CF_3$, $CF_3$, $CF_3$) |
| 188 | 2(n-$C_4H_9$, n-$C_4H_9$) | (H, F, H, H), (H, H, H, H) | ($CF_3$, $CF_3$, $CF_3$) |
| 189 | 2(n-$C_4H_9$, n-$C_4H_9$) | (Ph, H, H, H), (H, H, H, H) | ($CF_3$, $CF_3$, $CF_3$) |
| 190 | 2(n-$C_4H_9$, n-$C_4H_9$) | (H, Ph, H, H), (H, H, H, H) | ($CF_3$, $CF_3$, $CF_3$) |
| 191 | 2(n-$C_4H_9$, n-$C_4H_9$) | (Ac, H, H, H), (H, H, H, H) | ($CF_3$, $CF_3$, $CF_3$) |
| 192 | 2(n-$C_4H_9$, n-$C_4H_9$) | (H, Ac, H, H), (H, H, H, H) | ($CF_3$, $CF_3$, $CF_3$) |
| 193 | 2(n-$C_4H_9$, n-$C_4H_9$) | (CN, H, H, H), (H, H, H, H) | ($CF_3$, $CF_3$, $CF_3$) |
| 194 | 2(n-$C_4H_9$, n-$C_4H_9$) | (H, CN, H, H), (H, H, H, H) | ($CF_3$, $CF_3$, $CF_3$) |
| 195 | 2(n-$C_4H_9$, n-$C_4H_9$) | ($CH_3$, H, H, H), (H, H, H, H) | ($CH_3$, $CH_3$, $CH_3$) |
| 196 | 2(n-$C_4H_9$, n-$C_4H_9$) | ($CH_3$, H, H, H), (H, H, H, H) | ($C_6H_4CH_3$, $C_6H_4CH_3$, $C_6H_4CH_3$) |
| 197 | 2(n-$C_4H_9$, n-$C_4H_9$) | ($CH_3$, H, H, H), (H, H, H, H) | ($CF_3$, $CF_3$, $CF_3$) |
| 198 | 2(n-$C_4H_9$, n-$C_4H_9$) | ($CH_3$, H, H, H), (H, H, H, H) | ($CF_3$, $CF_3$, $CH_3$) |
| 199 | 2(n-$C_4H_9$, n-$C_4H_9$) | ($CH_3$, H, H, H), (H, H, H, H) | ($CF_3$, $CF_3$, $C_6H_4CH_3$) |
| 200 | 2(n-$C_4H_9$, n-$C_4H_9$) | ($CH_3$, H, H, H), (H, H, H, H) | ($CF_3$, $CH_3$, $C_6H_4CH_3$) |
| 201 | 2(n-$C_4H_9$, n-$C_4H_9$) | ($CH_3$, H, H, H), (H, H, H, H) | ($C_2F_5$, $C_2F_5$, $C_2F_5$) |
| 202 | 2(n-$C_4H_9$, n-$C_4H_9$) | ($CH_3$, H, H, H), (H, H, H, H) | ($C_2F_5$, $C_2F_5$, n-$C_4F_9$) |
| 203 | 2(n-$C_4H_9$, n-$C_4H_9$) | ($CH_3$, H, H, H), (H, H, H, H) | ($C_2F_5$, $C_2F_5$, $C_6F_5$) |
| 204 | 2(n-$C_4H_9$, n-$C_4H_9$) | ($CH_3$, H, H, H), (H, H, H, H) | ($C_2F_5$, $C_2F_5$, $C_6F_4CH_3$) |
| 205 | 2(n-$C_4H_9$, n-$C_4H_9$) | ($CH_3$, H, H, H), (H, H, H, H) | ($C_6F_4CH_3$, $C_6F_4CH_3$, $C_6F_4CH_3$) |

Compound 206

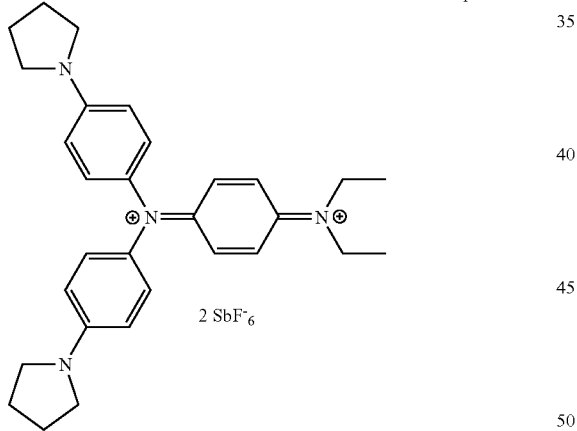

-continued

Compound 208

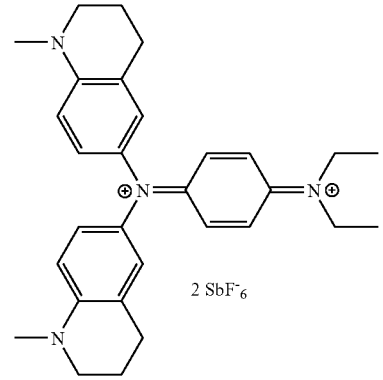

Compound 207

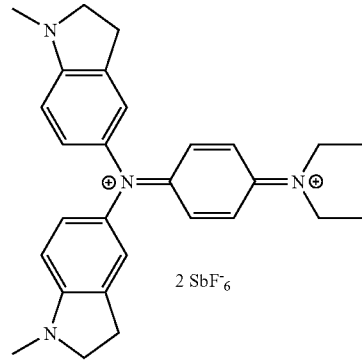

Compound 209

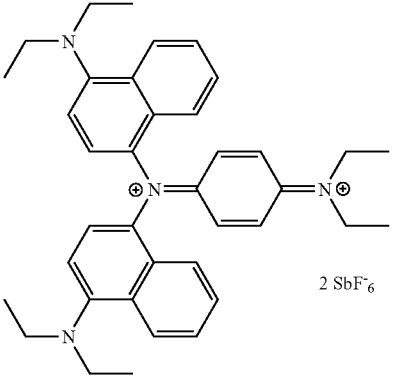

-continued
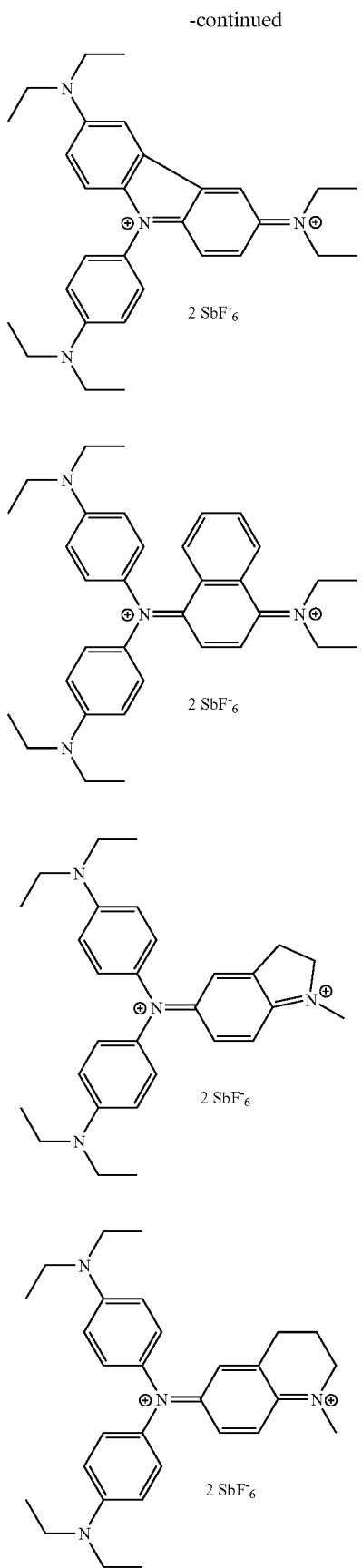
Compound 210
Compound 211
Compound 212
Compound 213
-continued
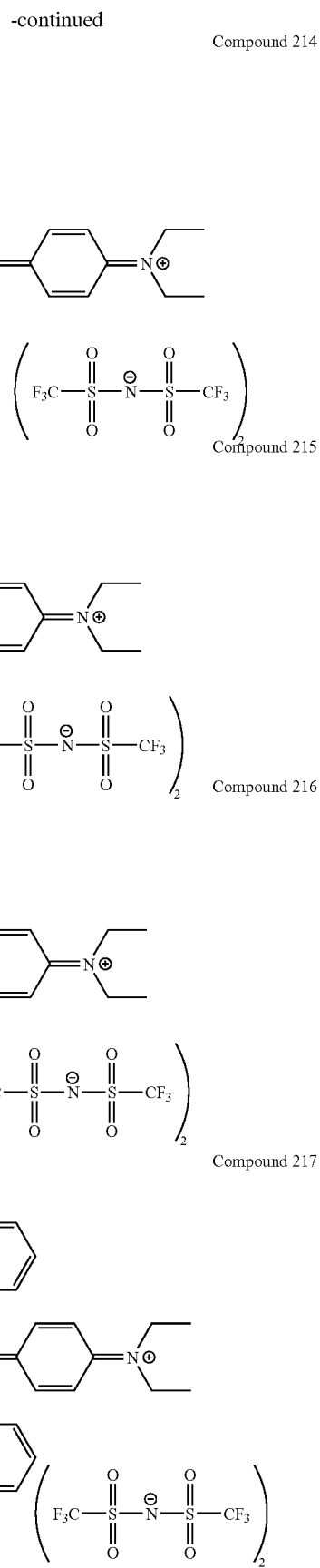
Compound 214
Compound 215
Compound 216
Compound 217

-continued
Compound 218
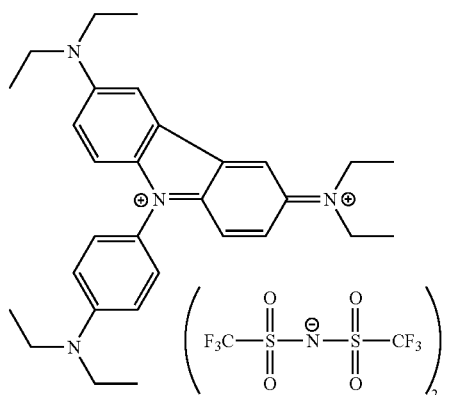
Compound 219
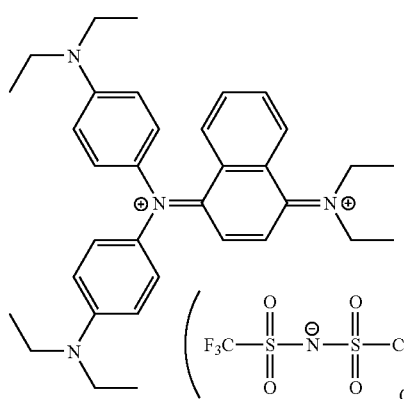
Compound 220
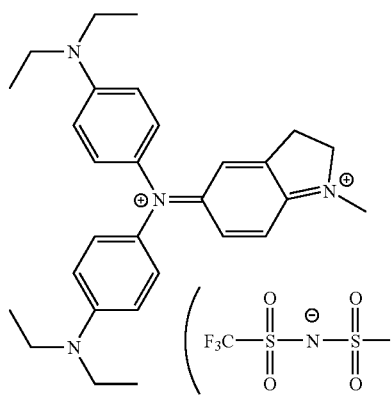
Compound 221
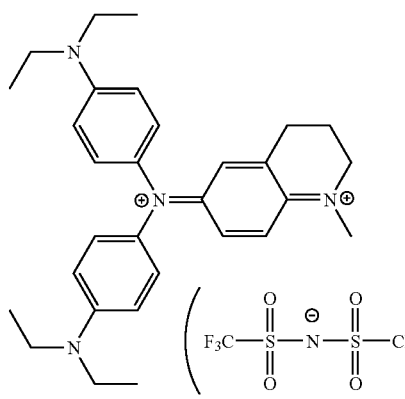
-continued
Compound 222
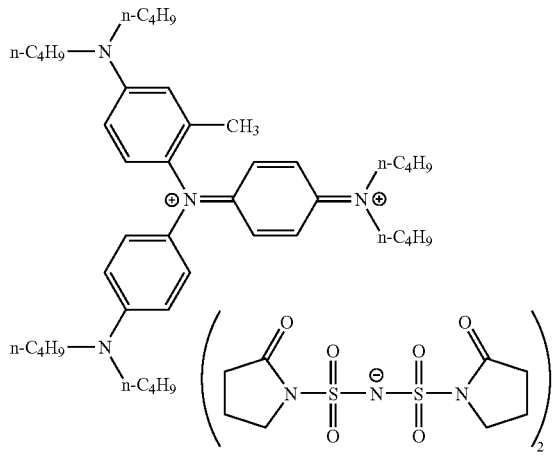
Compound 223
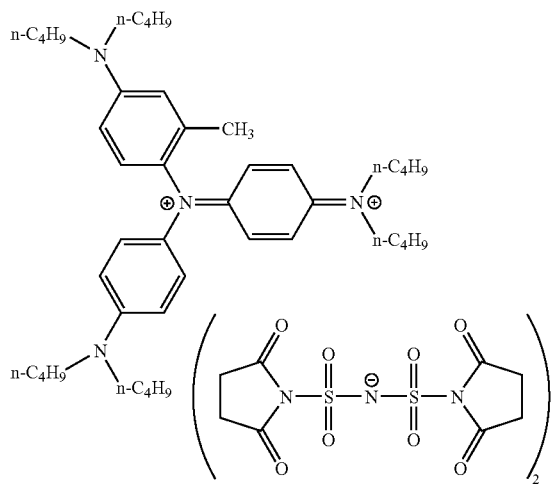
Compound 224
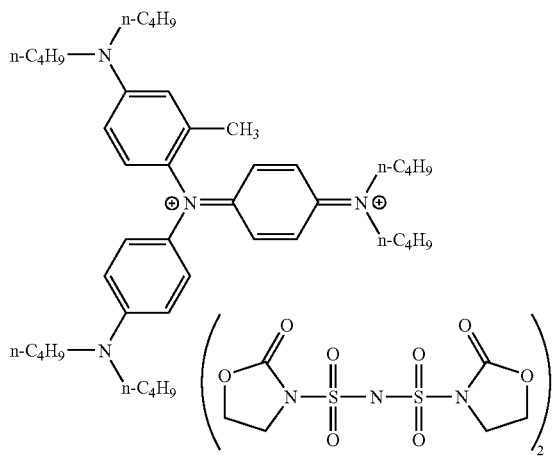

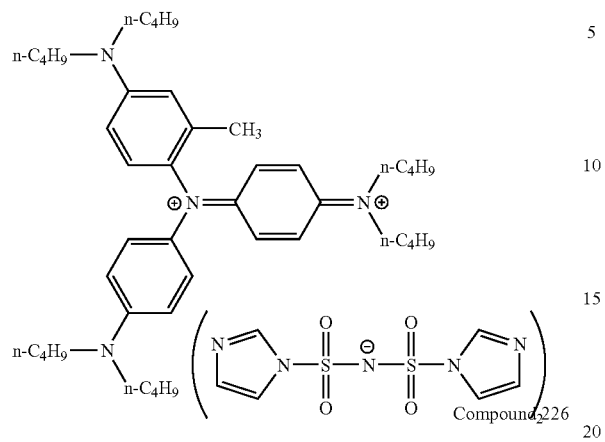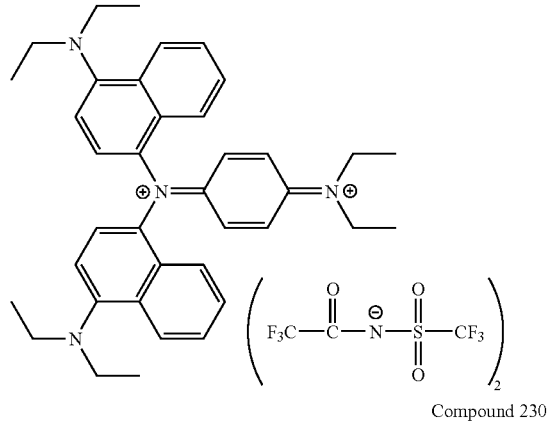

-continued
Compound 233
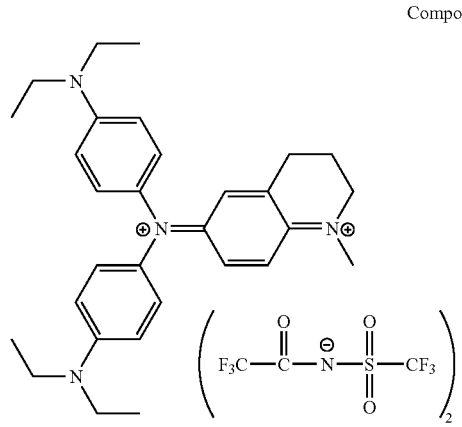
Compound 234
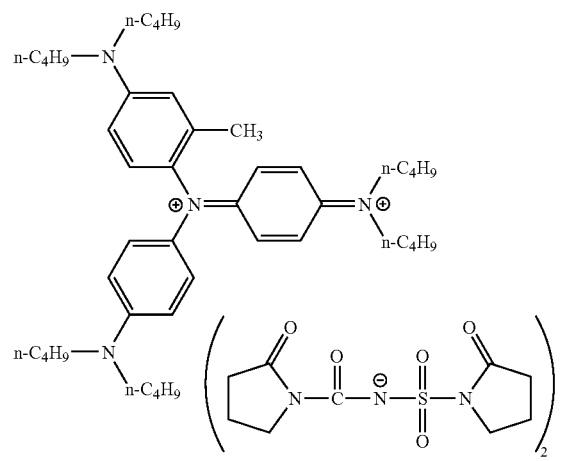
Compound 235
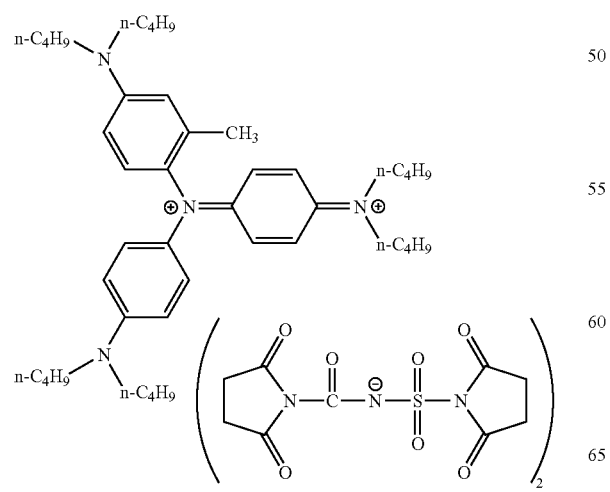
-continued
Compound 236
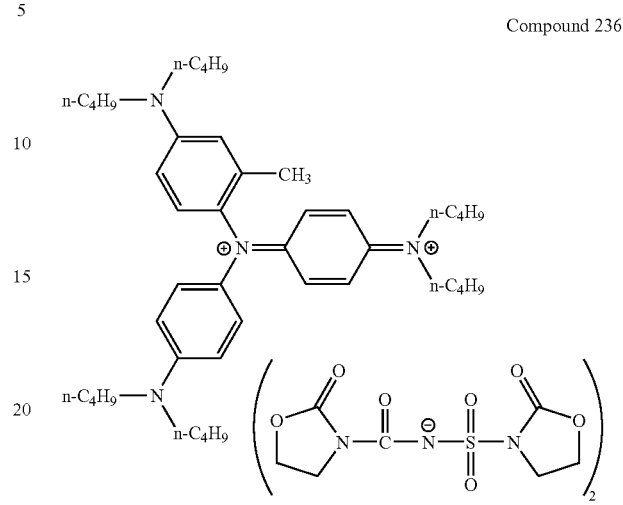
Compound 237
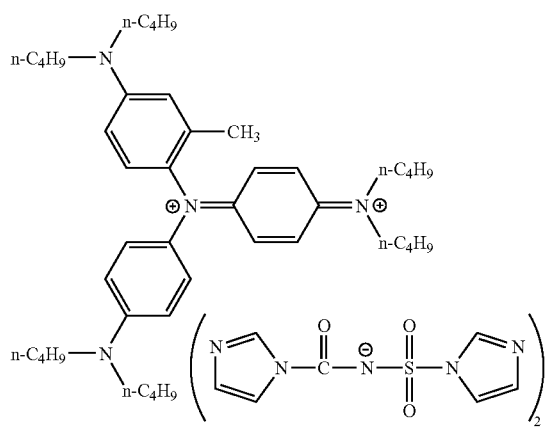
Compound 238
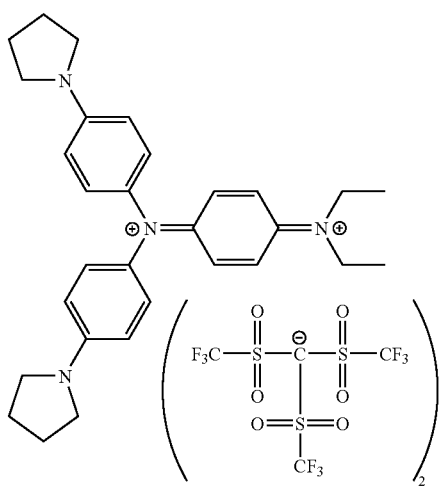

Compound 239
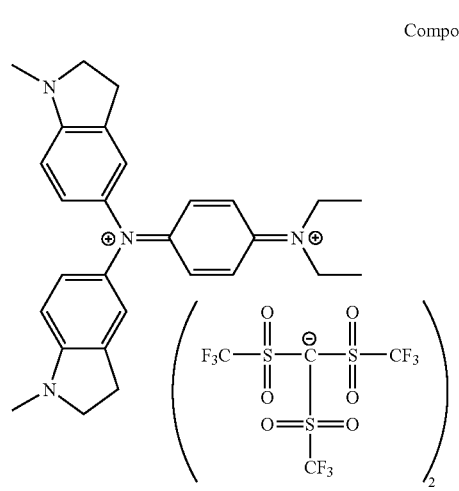
Compound 240
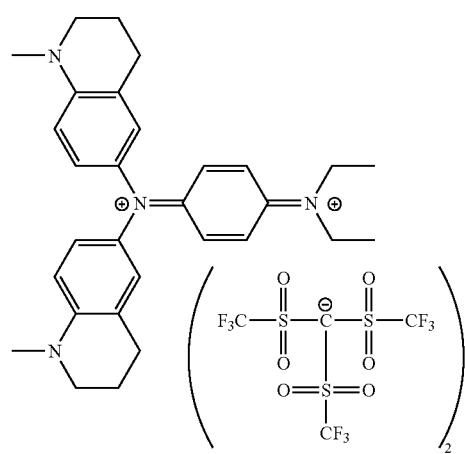
Compound 241
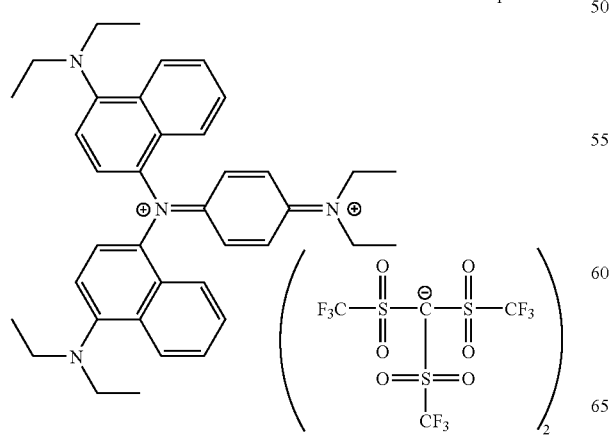
Compound 242
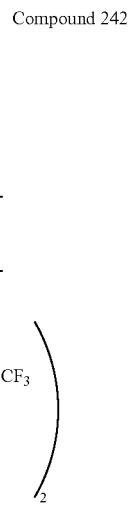
Compound 243
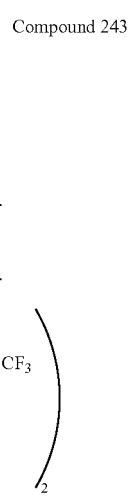
Compound 244

-continued

Compound 245

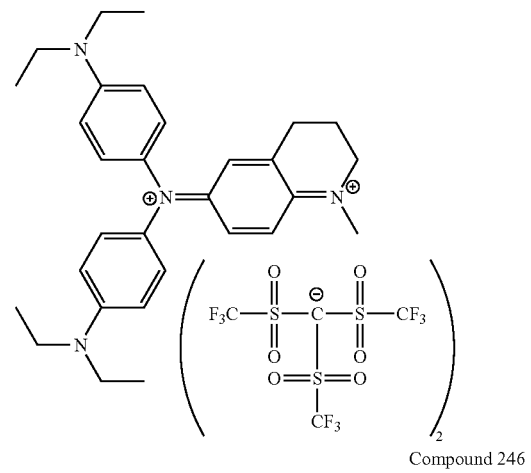

Compound 246

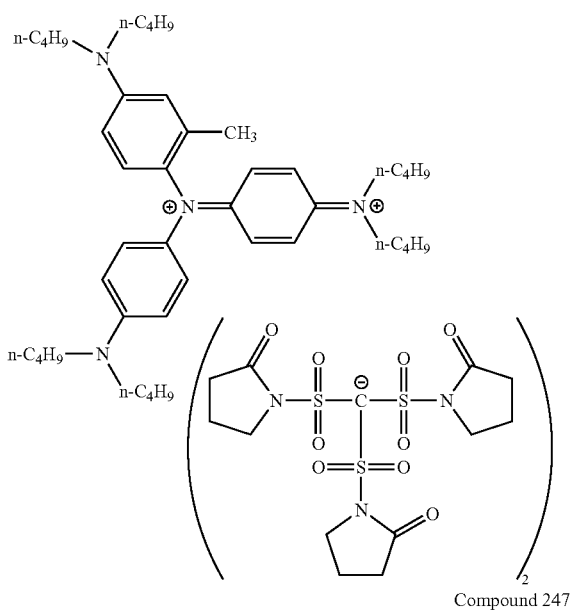

Compound 247

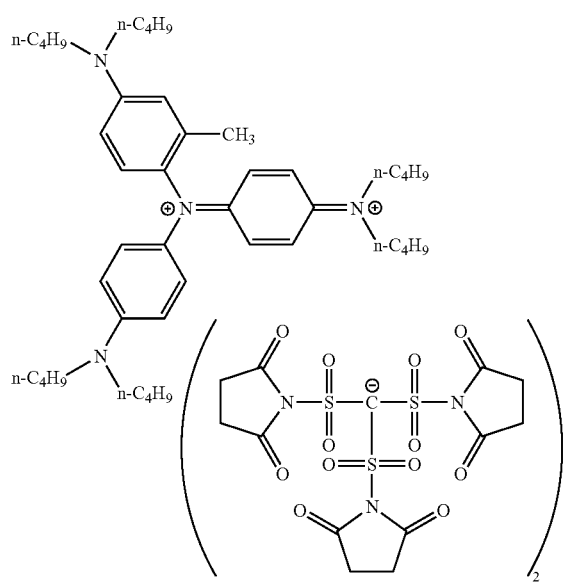

-continued

Compound 248

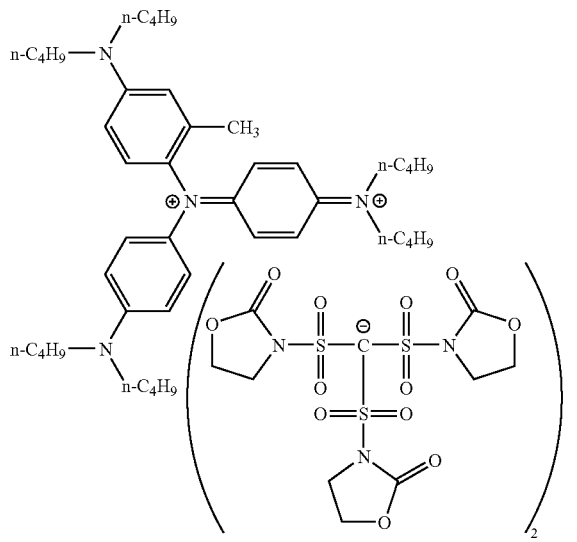

Compound 249

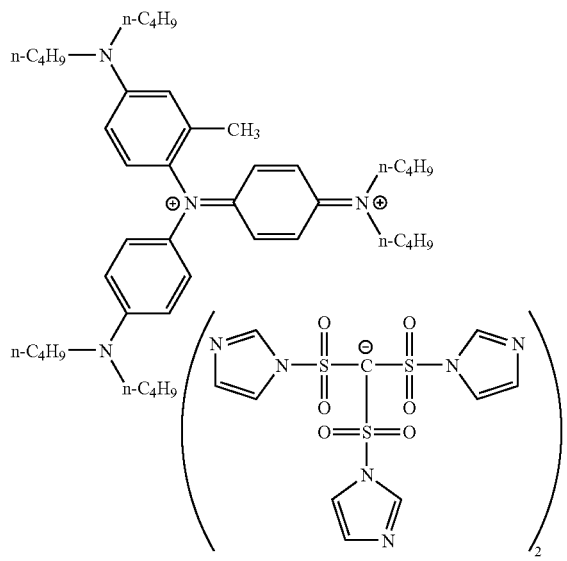

In the invention, the compound represented by Formula (I) may be synthesized, for example, by treating a compound represented by the following Formula (V) with a metal salt (preferably, a silver salt) of an inorganic acid or a metal salt (preferably, a silver salt) of an anion represented by any one of Formulae (II) to (IV) above.

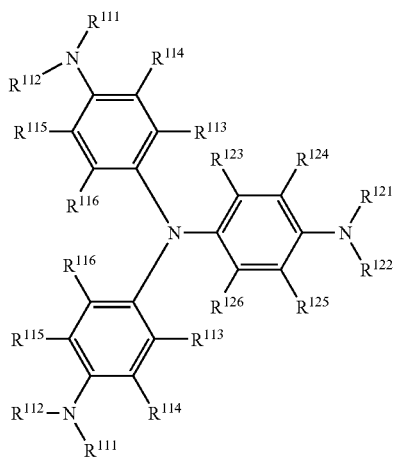

Formula (V)

In Formula (V), $R^{111}$ to $R^{116}$ and $R^{121}$ to $R^{126}$ have the same definitions as those of $R^{111}$ to $R^{116}$ and $R^{121}$ to $R^{126}$ in Formula (I).

The compound represented by Formula (V) may be synthesized, for example, based on the method described in Der Deutschen Chemischen Gesellschaft, vol. 92, pp. 245-251 (1959). The metal salt of an inorganic acid may be prepared by a common method, and silver salts of the compounds represented by Formulae (II) to (IV) may be synthesized based on, for example, the method described in JP-A No. 2006-143674.

In synthesis of the compound represented by Formula (I), as a ratio of raw materials used in the synthesis reaction, the silver salt of an inorganic acid or the sliver salt of a compound represented by any of Formula (II) to Formula (IV) is used at preferably from 0.1 to 10 moles, more preferably from 1 to 6 moles, further preferably from 1.5 to 5 moles, particularly preferably from 2 to 4 moles, with respect to 1 mole of the compound represented by Formula (V), whereby a compound represented by Formula (I) may be obtained.

Examples of the solvent used in the synthesis reaction include water, an amide solvent (e.g. N,N-dimethylformuamide, N,N-dimethylacetamide, 1-methyl-2-pyrrolidone), a sulfone solvent (e.g. sulfolane), a sulfoxide solvent (e.g. dimethyl sulfoxide), a ureide solvent (e.g. tetramethylurea), an ether solvent (e.g. dioxane, cyclopentyl methyl ether), a ketone solvent (e.g. acetone, cyclohexanone), a hydrocarbon solvent (e.g. toluene, xylene, n-decane), a halogen solvent (e.g. tetrachloroethane, chlorobenzene), an alcohol solvent (e.g. methanol, ethanol, isopropyl alcohol, ethylene glycol, cyclohexanol, phenol), a pyridine solvent (e.g. pyridine, γ-picoline, 2,6-lutidine), an ester solvent (e.g. ethyl acetate, butyl acetate), a carboxylic acid solvent (e.g. acetic acid, propionic acid) and a nitrile solvent (e.g. acetonitrile). In an embodiment, only a single solvent, which may be selected from the above, may be used. In another embodiment, two or more solvents, which may be selected from the above, may be used together.

Among these solvents, preferable examples include water, an amide solvent, a sulfone solvent, a sulfoxide solvent, a ureide solvent, a halogen solvent, an alcohol solvent, a pyridine solvent, an ester solvent, a carboxylic acid solvent and a nitrile solvent, more preferable examples include water, an amide solvent, a sulfone solvent, a ureide solvent, a halogen solvent, an alcohol solvent, an ester solvent and a nitrite solvent, and still more preferable examples include water, a sulfone solvent, an alcohol solvent, an ester solvent and a nitrile solvent. It is also preferable to use water and one or more other solvents together.

The reaction temperature may be from −30 to 250° C., preferably from −10 to 150° C., more preferably from −5 to 100° C., still more preferably from 0 to 70° C., further preferably 10 to 50° C. It is also preferable to initiate the reaction at a temperature of from −5 to 20° C., and then raise the reaction temperature to a range of from 25 to 100° C.

Since the triarylamide derivative represented by Formula (I) according to the invention is a near infrared absorbing diimmonium compound which is excellent in light resistance, wet heat resistance and solubility, it may be widely used, for example, in photopolymerization initiators and electrophotographic photoreceptors.

Exemplary embodiments of the invention include the following:

<1>. A triarylamine derivative represented by the following Formula (I):

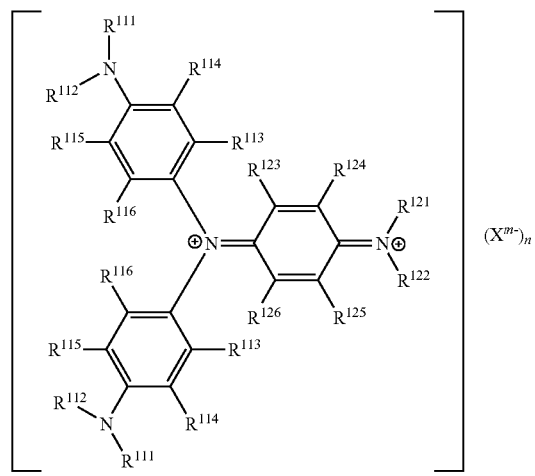

Formula (I)

wherein, in Formula (I): $R^{111}$, $R^{112}$, $R^{121}$ and $R^{122}$ each independently represent a hydrogen atom, an aliphatic group or an aromatic group, $R^{113}$, $R^{114}$, $R^{115}$, $R^{116}$, $R^{123}$, $R^{124}$, $R^{125}$ and $R^{126}$ each independently represent a hydrogen atom or a substituent, provided that at least one pair among $R^{111}$ and $R^{112}$, $R^{112}$ and $R^{122}$, $R^{113}$ and $R^{123}$, $R^{114}$ and $R^{124}$, $R^{115}$ and $R^{125}$, and $R^{116}$ and $R^{126}$ includes two different groups; at least one ring may be formed by mutual bonding in at least one pair among $R^{111}$ and $R^{112}$, $R^{111}$ and $R^{114}$, $R^{113}$ and $R^{114}$, $R^{113}$ and $R^{123}$, $R^{123}$ and $R^{124}$, $R^{121}$ and $R^{124}$, $R^{121}$ and $R^{122}$, and two $R^{116}$s which are respectively bound to different phenyl groups; $X^{m-}$ represents an m-valent anion; m and n represent 1 or 2; and a product of m and n is 2.

<2>. The triarylamine derivative as described in <1>, wherein at least one group among $R^{111}$, $R^{112}$, $R^{121}$ and $R^{122}$ in Formula (I) is different from a remainder of these groups.

<3>. The triarylamine derivative as described in <1>, wherein at least one group among $R^{113}$, $R^{114}$, $R^{115}$, $R^{116}$, $R^{123}$, $R^{124}$, $R^{125}$ and $R^{126}$ in Formula (I) is different from a remainder of these groups.

<4>. The triarylamine derivative as described in <1>, wherein $R^{111}$, $R^{112}$, $R^{121}$ and $R^{122}$ each independently represent a substituted or unsubstituted alkyl group having a total carbon number of from 2 to 6.

<5>. The triarylamine derivative as described in <1>, wherein at least one ring is formed by mutual bonding in at least one pair among $R^{111}$ and $R^{112}$, $R^{111}$ and $R^{114}$ $R^{113}$ and $R^{114}$, $R^{113}$ and $R^{123}$, $R^{123}$ and $R^{124}$, $R^{121}$ and $R^{124}$, $R^{121}$ and $R^{122}$ and two $R^{116}$s which are respectively bound to different phenyl groups.

<6>. The triarylamine derivative as described in <1>, wherein $X^{m-}$ in Formula (I) represents a perchlorate ion, a hexafluoroantimonate ion, a hexafluorophosphate ion, a tetrafluoroborate ion or an anion represented by any of the following Formulae (II) to (IV):

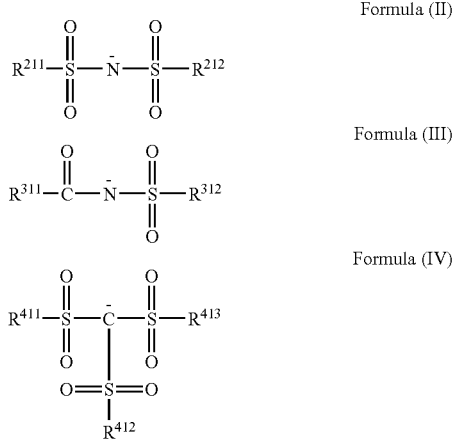

wherein, in Formulae (II) to (IV), $R^{211}$, $R^{212}$, $R^{311}$, $R^{312}$, $R^{411}$, $R^{412}$ and $R^{413}$ each independently represent an aliphatic group, an aromatic group or a heterocyclic group.

<7>. The triarylamine derivative as described in <6>, wherein $X^{m-}$ in Formula (I) represents an anion represented by any of Formula (II) to Formula (IV), and $R^{211}$, $R^{212}$, $R^{311}$, $R^{312}$, $R^{411}$, $R^{412}$ and $R^{413}$ each independently represent an aliphatic group having a halogen atom, an aromatic group having a halogen atom or a heterocyclic group having a halogen atom.

<8>. The triarylamine derivative as described in <7>, wherein $R^{211}$, $R^{212}$, $R^{311}$, $R^{312}$, $R^{411}$, $R^{412}$ and $R^{413}$ in Formulae (II) to (IV) represent an aliphatic group having a fluorine atom, an aromatic group having a fluorine atom, or a heterocyclic group having a fluorine atom.

<9>. The triarylamine derivative as described in <6>, wherein $R^{211}$, $R^{212}$, $R^{311}$, $R^{312}$, $R^{411}$, $R^{412}$ and $R^{413}$ each independently represent an alkyl group having 1 to 6 carbon atoms.

<10>. The triarylamine derivative as described in <6>, wherein $R^{111}$, $R^{112}$, $R^{121}$ and $R^{122}$ each independently represent a hydrogen atom, an alkyl group, or an aryl group, one or two groups selected from $R^{111}$, $R^{112}$, $R^{121}$ and $R^{122}$ each independently represent a different group from a remainder of these groups, $R^{211}$, $R^{212}$, $R^{311}$, $R^{312}$, $R^{411}$, $R^{412}$ and $R^{413}$ each independently represent a hydrogen atom, an alkyl group, an aryl group, or a substituent, and $X^{m-}$ represents a perchlorate ion, a hexafluoroantimonate ion, a hexafluorophosphate ion, a tetrafluoroborate ion, or an anion represented by any of Formulae (II) to (IV).

<11>. The triarylamine derivative as described in <6>, wherein $R^{111}$, $R^{112}$, $R^{121}$ and $R^{122}$ each independently represent a hydrogen atom, an alkyl group, or an aryl group, $R^{211}$, $R^{212}$, $R^{311}$, $R^{312}$, $R^{411}$, $R^{412}$ and $R^{413}$ each independently represent a hydrogen atom, an alkyl group, an aryl group, or a substituent, one group selected from $R^{211}$, $R^{212}$, $R^{311}$, $R^{312}$, $R^{411}$, $R^{412}$ and $R^{413}$ is a different group from a remainder of these groups, and $X^{m-}$ represents a perchlorate ion, a hexafluoroantimonate ion, a hexafluorophosphate ion, a tetrafluoroborate ion, or an anion represented by any of Formulae (II) to (IV).

<12>. The triarylamine derivative as described in <6>, wherein $R^{111}$, $R^{112}$, $R^{121}$ and $R^{122}$ each independently represent an alkyl group, one or two groups selected from $R^{111}$, $R^{112}$, $R^{121}$ and $R^{122}$ each independently represent a different group from a remainder of these groups, $R^{211}$, $R^{212}$, $R^{311}$, $R^{312}$, $R^{411}$, $R^{412}$ and $R^{413}$ each independently represent a hydrogen atom, and $X^{m-}$ is an anion represented by any one of Formulae (II) to (IV).

<13>. The triarylamine derivative as described in <6>, wherein $R^{111}$, $R^{112}$, $R^{121}$ and $R^{122}$ each independently represent an alkyl group, $R^{211}$, $R^{212}$, $R^{311}$, $R^{312}$, $R^{411}$, $R^{412}$ and $R^{413}$ each independently represent a hydrogen atom, an alkyl group, an aryl group, an alkoxy group, a cyano group, or an acyl group, one group selected from $R^{211}$, $R^{212}$, $R^{311}$, $R^{312}$, $R^{411}$, $R^{412}$ and $R^{413}$ is a different group from a remainder of these groups, and $X^{m-}$ is an anion represented by any of Formula (II) to Formula (IV).

EXAMPLES

The present invention will be more specifically explained below by way of Examples, but the invention is not limited to these Examples. Unless otherwise is indicated, "part" and "%" are based on mass.

Example 1

Synthesis of Compound 6

Into 40 ml of DMF was completely dissolved 5 g of bis(4-di(n-butyl)aminophenyl)-4-diethylaminophenylamine, and the solution was heated and stirred at 60° C. To this was added 15 g of silver hexafluoroantimonate, and the mixture was heated and stirred at 60° C. for 3 hours. The reaction solution was filtered to remove insoluble components, 200 ml of water was added to the reaction solution, and precipitated crystal was collected by filtration. The resulting crystal was washed with water, and dried to obtain 8.3 g (91%) of a target compound 6.

When a mass spectrum was measured, M+ was 571. When an absorption spectrum was measured, a maximum absorption wavelength was λmax=916 nm (dichloromethane). Results of elemental analysis are shown in Table 9.

Example 2

Synthesis of Compound 7

Into 40 ml of DMF was completely dissolved 5 g of bis(4-di(iso-butyl)aminophenyl)-4-diethylaminophenylamine, and the solution was heated and stirred at 60° C. To this was added 15 g of silver hexafluoroantimonate, and the mixture was heated and stirred at 60° C. for 3 hours. The reaction solution was filtered to remove insoluble components, 200 ml of water was added to the reaction solution, and precipitated crystal was collected by filtration. The resulting crystal was washed with water, and dried to obtain 8.1 g (89%) of a target compound 7.

When a mass spectrum was measured, M⁺ was 571. When an absorption spectrum was measured, a maximum absorption wavelength was λmax=917 nm (dichloromethane).

Results of elemental analysis are shown in Table 9.

Example 3

Synthesis of Compound 28

Into 40 ml of DMF was completely dissolved 5 g of bis(4-di(n-butyl)aminophenyl)-4-di(n-butyl)amino-2-methylphenylamine, and the solution was heated and stirred at 60° C. To this was added 15 g of silver hexafluoroantimonate, and the mixture was heated and stirred at 60° C. for 3 hours. The reaction solution was filtered to remove insoluble components, 200 ml of water was added to the reaction solution, and precipitated crystal was collected by filtration. The resulting crystal was washed with water, and dried to obtain 7.6 g (92%) of a target compound 28.

When a mass spectrum was measured, M⁺ was 641. When an absorption spectrum was measured, a maximum absorption wavelength was λmax=916 nm (dichloromethane).

Results of elemental analysis are shown in Table 9.

Example 4

Synthesis of Compound 32

Into 40 ml of DMF was completely dissolved 5 g of bis(4-di(n-butyl)aminophenyl)-4-di(n-butyl)amino-2-methoxyphenylamine, and the solution was heated and stirred at 60° C. To this was added 15 g of silver hexafluoroantimonate, and the mixture was heated and stirred at 60° C. for 3 hours. The reaction solution was filtered to remove insoluble components, 200 ml of water was added to the reaction solution, and precipitated crystal was collected by filtration. The resulting crystal was washed with water, and dried to obtain 7.2 g (85%) of a target compound 32. When a mass spectrum was measured, M⁺ was 657. When an absorption spectrum was measured, a maximum absorption wavelength was λmax=924 nm (dichloromethane). Results of elemental analysis are shown in Table 9.

Example 5

Synthesis of Compound 34

Into 40 ml of DMF was completely dissolved 5 g of bis(4-di(n-butyl)aminophenyl)-2-chloro-4-di(n-butyl)aminophenylamine, and the solution was heated and stirred at 60° C. To this was added 15 g of silver hexafluoroantimonate, and the mixture was heated and stirred at 60° C. for 3 hours. The reaction solution was filtered to remove insoluble components, 200 ml of water was added to the reaction solution, and precipitated crystal was collected by filtration. The resulting crystal was washed with water, and dried to obtain 7.0 g (82%) of a target compound 34.

When a mass spectrum was measured, M⁺ was 661. When an absorption spectrum was measured, a maximum absorption wavelength was λmax=914 nm (dichloromethane).

Results of elemental analysis are shown in Table 9.

Example 6

Synthesis of Compound 44

Into 40 ml of DMF was completely dissolved 5 g of bis(4-di(n-butylaminophenyl)-4-di(n-butyl)-2-methylaminophenylamine, and the solution was heated and stirred at 60° C. To this was added 15 g of silver perchlorate, and the mixture was heated and stirred at 60° C. for 3 hours. The reaction solution was filtered to remove insoluble components, 200 ml of water was added to the reaction solution, and precipitated crystal was collected by filtration. Resulting crystal was washed with water, and dried to obtain 6.2 g (95%) of a target compound 44.

When a mass spectrum was measured M⁺ was 641. When an absorption spectrum was measured, a maximum absorption wavelength was λmax=916 nm (dichloromethane).

Results of elemental analysis are shown in Table 9.

Example 7

Synthesis of Compound 45

Into 40 ml of DMF was completely dissolved 5 g of bis(4-di(n-butyl)aminophenyl)-4-di(n-butyl)-2-methylaminophenylamine, and the solution was heated and stirred at 60° C. To this was added 15 g of silver hexafluorophosphate, and the mixture was heated and stirred at 60° C. for 3 hours. The reaction solution was filtered to remove insoluble components, 200 ml of water was added to the reaction solution, and precipitated crystal was collected by filtration. Resulting crystal was washed with water, and dried to obtain 6.7 g (93%) of a target compound 45.

When a mass spectrum was measured, M⁺ was 641. When an absorption spectrum was measured, a maximum absorption wavelength was λmax=916 nm (dichloromethane).

Results of elemental analysis are shown in Table 9.

Example 8

Synthesis of Compound 46

Into 40 ml of DMF was completely dissolved 5 g of bis(4-di(n-butyl)aminophenyl)-4-di(n-butyl)-2-methylaminophenylamine, and the solution was heated and stirred at 60° C. To this was added 15 g of silver nitrate, and the mixture was heated and stirred at 60° C. for 3 hours. The reaction solution was filtered to remove insoluble components, 200 ml of water was added to the reaction solution, and precipitated crystal was collected by filtration. Resulting crystal was washed with water, and dried to obtain 5.3 g (90%) of a target compound 46.

When a mass spectrum was measured, M⁺ was 641. When an absorption spectrum was measured, a maximum absorption wavelength was λmax=916 nm (dichloromethane).

Results of elemental analysis are shown in Table 9.

Example 9

Synthesis of Compound 47

Into 40 ml of DMF was completely dissolved 5 g of bis(4-di(n-butyl)aminophenyl)-4-di(n-butyl)-2-methylaminophenylamine, and the solution was heated and stirred at 60° C. To this was added 15 g of silver paratoluenesulfonate, and the mixture was heated and stirred at 60° C. for 3 hours. The reaction solution was filtered to remove insoluble components, 200 ml of water was added to the reaction solution, and precipitated crystal was collected by filtration. Resulting crystal was washed with water, and dried to obtain 5.5 g (87%) of a target compound 47.

When a mass spectrum was measured, M+ was 641. When an absorption spectrum was measured, a maximum absorption wavelength was λmax=916 nm (dichloromethane).

Results of elemental analysis are shown in Table 9.

Example 10

Synthesis of Compound 48

Into 40 ml of DMF was completely dissolved 5 g of bis(4-di(n-butyl)aminophenyl)-4-di(n-butyl)-2-methylaminophenylamine, and the solution was heated and stirred at 60° C. To this was added 15 g of silver trifluoromethanesulfonate, and the mixture was heated and stirred at 60° C. for 3 hours. The reaction solution was filtered to remove insoluble components, 200 ml of water was added to the reaction solution, and precipitated crystal was collected by filtration. Resulting crystal was washed with water, and dried to obtain 6.6 g (90%) of a target compound 48.

When a mass spectrum was measured, M+ was 641. When an absorption spectrum was measured, a maximum absorption wavelength was λmax=916 nm (dichloromethane).

Results of elemental analysis are shown in Table 9.

Example 11

Synthesis of Compound 56

Into 40 ml of DMF was completely dissolved 5 g of bis(4-di(n-butyl)aminophenyl)-4-diethylaminophenylamine, and the solution was heated and stirred at 60° C. To this was added 12 g of a silver salt of bis(trifluoromethanesulfonyl)imide, and the mixture was heated and stirred at 60° C. for 3 hours. The reaction solution was filtered to remove insoluble components, 200 ml of water was added to the reaction solution, and precipitated crystal was collected by filtration. Resulting crystal was washed with water, and dried to obtain 6.8 g (85%) of a target compound 56.

When a mass spectrum was measured, M+ was 571. When an absorption spectrum was measured, a maximum absorption wavelength was λmax=916 nm (dichloromethane).

Results of elemental analysis are shown in Table 9.

Example 12

Synthesis of Compound 57

Into 40 ml of DMF was completely dissolved 5 g of bis(4-di(iso-butyl)aminophenyl)-4-diethylaminophenylamine, and the solution was heated and stirred at 60° C. To this was added 12 g of a silver salt of bis(trifluoromethanesulfonyl)imide, and the mixture was heated and stirred at 60° C. for 3 hours. The reaction solution was filtered to remove insoluble components, 200 ml of water was added to the reaction solution, and precipitated crystal was collected by filtration. Resulting crystal was washed with water, and dried to obtain 7.0 g (87%) of a target compound 57.

When a mass spectrum was measured, M+ was 571. When an absorption spectrum was measured, a maximum absorption wavelength was λmax=917 nm (dichloromethane).

Results of elemental analysis are shown in Table 9.

Example 13

Synthesis of Compound 79

Into 40 ml of DMF was completely dissolved 5 g of bis(4-di(n-butyl)aminophenyl)-4-di(n-butyl)amino-2-methylphenylamine, and the solution was heated and stirred at 60° C. To this was added 12 g of a silver salt of bis(trifluoromethanesulfonyl)imide, and the mixture was heated and stirred at 60° C. for 3 hours. The reaction solution was filtered to remove insoluble components, 200 ml of water was added to the reaction solution, and precipitated crystal was collected by filtration. Resulting crystal was washed with water, and dried to obtain 6.9 g (90%) of a target compound 79.

When a mass spectrum was measured, M+ was 641. When an absorption spectrum was measured, a maximum absorption wavelength was λmax=916 nm (dichloromethane).

Results of elemental analysis are shown in Table 9.

Example 14

Synthesis of Compound 83

Into 40 ml of DMF was completely dissolved 5 g of bis(4-di(n-butyl)aminophenyl)-4-di(n-butyl)amino-2-methoxyphenylamine, and the solution was heated and stirred at 60° C. To this was added 12 g of a silver salt of bis(trifluoromethanesulfonyl)imide, and the mixture was heated and stirred at 60° C. for 3 hours. The reaction solution was filtered to remove insoluble components, 200 ml of water was added to the reaction solution, and precipitated crystal was collected by filtration. Resulting crystal was washed with water, and dried to obtain 7.0 g (92%) of a target compound 83.

When a mass spectrum was measured, M+ was 657. When an absorption spectrum was measured, a maximum absorption wavelength was λmax=924 nm (dichloromethane).

Results of elemental analysis are shown in Table 9.

Example 15

Synthesis of Compound 85

Into 40 ml of DMF was completely dissolved 5 g of bis(4-di(n-butyl)aminophenyl)-2-chloro-4-di(n-butyl)aminophenylamine, and the solution was heated and stirred at 60° C. To this was added 12 g of a silver salt of bis(trifluoromethanesulfonyl)imide, and the mixture was heated and stirred at 60° C. for 3 hours. The reaction solution was filtered to remove insoluble components, 200 ml of water was added to the reaction solution, and precipitated crystal was collected by filtration. Resulting crystal was washed with water, and dried to obtain 7.0 g (92%) of a target compound 85.

When a mass spectrum was measured, M+ was 661. When an absorption spectrum was measured, a maximum absorption wavelength was λmax=914 nm (dichloromethane).

Results of elemental analysis are shown in Table 9.

Example 16

Synthesis of Compound 106

Into 40 ml of DMF was completely dissolved 5 g of bis(4-di(n-butyl)aminophenyl)-4-diethylaminophenylamine, and the solution was heated and stirred at 60° C. To this was added 12 g of a silver salt of N-trifluoroacetyl-N-trifluoromethanesulfonylimide, and the mixture was heated and stirred at 60° C. for 3 hours. The reaction solution was filtered to remove insoluble components, 200 ml of water was added to the reaction solution, and precipitated crystal was collected by filtration. Resulting crystal was washed with water, and dried to obtain 6.6 g (90%) of a target compound 106.

When a mass spectrum was measured, M⁺ was 571. When an absorption spectrum was measured, a maximum absorption wavelength was λmax=916 nm (dichloromethane).

Results of elemental analysis are shown in Table 9

Example 17

Synthesis of Compound 107

Into 40 ml of DMF was completely dissolved 5 g of bis(4-di(iso-butyl)aminophenyl)-4-diethylaminophenylamine, and the solution was heated and stirred at 60° C. To this was added 12 g of a silver salt of N-trifluoroacetyl-N-trifluoromethanesulfonylimide, and the mixture was heated and stirred at 60° C. for 3 hours. The reaction solution was filtered to remove insoluble components, 200 ml of water was added to the reaction solution, and precipitated crystal was collected by filtration. Resulting crystal was washed with water, and dried to obtain 6.3 g (86%) of a target compound 107.

When a mass spectrum was measured, M⁺ was 571. When an absorption spectrum was measured, a maximum absorption wavelength was λmax=917 nm (dichloromethane).

Results of elemental analysis are shown in Table 9.

Example 18

Synthesis of Compound 129

Into 40 ml of DMF was completely dissolved 5 g of bis(4-di(n-butyl)aminophenyl)-4-di(n-butyl)amino-2-methylphenylamine, and the solution was heated and stirred at 60° C. To this was added 12 g of a silver salt of N-trifluoroacetyl-N-trifluoromethanesulfonylimide, and the mixture was heated and stirred at 60° C. for 3 hours. The reaction solution was filtered to remove insoluble components, 200 ml of water was added to the reaction solution, and precipitated crystal was collected by filtration. Resulting crystal was washed with water, and dried to obtain 6.4 g (91%) of a target compound 129.

When a mass spectrum was measured, M⁺ was 641. When an absorption spectrum was measured, a maximum absorption wavelength was λmax=916 nm (dichloromethane).

Results of elemental analysis are shown in Table 9.

Example 19

Synthesis of Compound 133

Into 40 ml of DMF was completely dissolved 5 g of bis(4-di(n-butyl)aminophenyl)-4-di(n-butyl)amino-2-methoxyphenylamine, and the solution was heated and stirred at 60° C. To this was added 12 g of a silver salt of N-trifluoroacetyl-N-trifluoromethanesulfonylimide, and the mixture was heated and stirred at 60° C. for 3 hours. The reaction solution was filtered to remove insoluble components, 200 ml of water was added to the reaction solution, and precipitated crystal was collected by filtration. Resulting crystal was washed with water, and dried to obtain 6.5 g (93%) of a target compound 133.

When a mass spectrum was measured, M⁺ was 657. When an absorption spectrum was measured, a maximum absorption wavelength was λmax 924 nm (dichloromethane).

Results of elemental analysis are shown in Table 9.

Example 20

Synthesis of Compound 135

Into 40 μl of DMF was completely dissolved 5 g of bis(4-di(n-butyl)aminophenyl)-2-chloro-4-di(n-butyl)aminophenylamine, and the solution was heated and stirred at 60° C. To this was added 12 g of a silver salt of N-trifluoroacetyl-N-trifluoromethanesulfonylimide, and the mixture was heated and stirred at 60° C. for 3 hours. The reaction solution was filtered to remove insoluble components, 200 ml of water was added to the reaction solution, and precipitated crystal was collected by filtration. Resulting crystal was washed with water, and dried to obtain 5.9 g (84%) of a target compound 135.

When a mass spectrum was measured, M⁺ was 661. When an absorption spectrum was measured, a maximum absorption wavelength was λmax=914 nm (dichloromethane).

Results of elemental analysis are shown in Table 9.

Example 21

Synthesis of Compound 156

Into 40 ml of DMF was completely dissolved 5 g of bis(4-di(n-butyl)aminophenyl)-(4-diethylaminophenyl)amine, and the solution was heated and stirred at 60° C. To this was added 12 g of tris(trifluoromethanesulfonyl)methyl silver, and the mixture was heated and stirred at 60° C. for 3 hours. The reaction solution was filtered to remove insoluble components, 200 ml of water was added to the reaction solution, and precipitated crystal was collected by filtration. Resulting crystal was washed with water, and dried to obtain 8.1 g (90%) of a target compound 156.

When a mass spectrum was measured, M⁺ was 571. When an absorption spectrum was measured, a maximum absorption wavelength was λmax=916 nm (dichloromethane).

Results of elemental analysis are shown in Table 9.

Example 22

Synthesis of Compound 157

Into 40 ml of DMF was completely dissolved 5 g of bis(4-di(iso-butyl)aminophenyl)-4-diethylaminophenylamine, and the solution was heated and stirred at 60° C. To this was added 12 g of tris(trifluoromethanesulfonyl)methyl silver, and the mixture was heated and stirred at 60° C. for 3 hours. The reaction solution was filtered to remove insoluble components, 200 ml of water was added to the reaction solution, and precipitated crystal was collected by filtration. Resulting crystal was washed with water, and dried to obtain 8.2 g (92%) of a target compound 157.

When a mass spectrum was measured, M⁺ was 571. When an absorption spectrum was measured, a maximum absorption wavelength was λmax=917 nm (dichloromethane).

Results of elemental analysis are shown in Table 9.

Example 23

Synthesis of Compound 179

Into 40 ml of DMF was completely dissolved 5 g of bis(4-di(n-butyl)aminophenyl)-4-di(n-butyl)amino-2-methylphenylamine, and the solution was heated and stirred at 60° C. To this was added 12 g of tris(trifluoromethanesulfonyl)methyl silver, and the mixture was heated and stirred at 60° C. for 3 hours. The reaction solution was filtered to remove insoluble components, 200 ml of water was added to the reaction solution, and precipitated crystal was collected by filtration. Resulting crystal was washed with water, and dried to obtain 8.1 g (95%) of a target compound 179.

When a mass spectrum was measured, Me was 641. When an absorption spectrum was measured, a maximum absorption wavelength was λmax=916 nm (dichloromethane).

Results of elemental analysis are shown in Table 9.

Example 25

Synthesis of Compound 185

Into 40 ml of DMF was completely dissolved 5 g of bis(4-di(n-butyl)aminophenyl)-2-chloro-4-di(n-butyl)aminophenylamine, and the solution was heated and stirred at 60° C. To this was added 12 g of tris(trifluoromethanesulfonyl)methyl silver, and the mixture was heated and stirred at 60° C. for 3 hours. The reaction solution was filtered to remove insoluble components, 200 ml of water was added to the reaction solution, and precipitated crystal was collected by filtration. Resulting crystal was washed with water, and dried to obtain 7.7 g (91%) of a target compound 185.

When a mass spectrum was measured, $M^+$ was 661. When an absorption spectrum was measured, a maximum absorption wavelength was λmax=914 nm (dichloromethane).

Results of elemental analysis are shown in Table 9.

TABLE 9

|  |  | Theoretical value | Measured value |
|---|---|---|---|
| Example 1 | Compound 6 | C, 43.78%%; H, 5.61%; N, 5.37% | C, 43.70%; H, 5.67%; N, 5.32% |
| Example 2 | Compound 7 | C, 43.78%; H, 5.61%; N, 5.37% | C, 43.76%; H, 5.69%; N, 5.34% |
| Example 3 | Compound 28 | C, 46.42%; H, 6.16%; N, 5.04% | C, 46.40%; H, 6.20%; N, 5.01% |
| Example 4 | Compound 32 | C, 45.76%; H, 6.07%; N, 4.96% | C, 45.72%; H, 6.09%; N, 4.91% |
| Example 5 | Compound 34 | C, 44.53%; H, 5.78%; N, 4.95% | C, 44.50%; H, 5.81%; N, 4.90% |
| Example 6 | Compound 44 | C, 61.49%; H, 8.16%; N, 6.67% | C, 61.44%; H, 8.20%; N, 6.65% |
| Example 7 | Compound 45 | C, 55.48%; H, 7.36%; N, 6.02% | C, 55.45%; H, 7.40%; N, 6.05% |
| Example 8 | Compound 46 | C, 67.51%; H, 8.96%; N, 10.99% | C, 67.47%; H, 9.02%; N, 10.91% |
| Example 9 | Compound 47 | C, 69.62%; H, 8.40%; N, 5.70% | C, 69.59%; H, 8.46%; N, 5.64% |
| Example 10 | Compound 48 | C, 57.55%; H, 7.30%; N, 5.97% | C, 57.50%; H, 7.35%; N, 5.91% |
| Example 11 | Compound 56 | C, 44.59%; H, 5.17%; N, 7.43% | C, 44.54%; H, 5.20%; N, 7.38% |
| Example 12 | Compound 57 | C, 44.59%; H, 5.17%; N, 7.43% | C, 44.54%; H, 5.11%; N, 7.40% |
| Example 13 | Compound 79 | C, 46.99%; H, 5.71%; N, 7.00% | C, 46.92%; H, 5.79%; N, 6.95% |
| Example 14 | Compound 83 | C, 46.37%; H, 5.63%; N, 6.90% | C, 46.31%; H, 5.66%; N, 6.86% |
| Example 15 | Compound 85 | C, 45.22%; H, 5.36%; N, 6.88% | C, 45.18%; H, 5.41%; N, 6.85% |
| Example 16 | Compound 106 | C, 49.90%; H, 5.52%; N, 7.94% | C, 49.82%; H, 5.56%; N, 7.89% |
| Example 17 | Compound 107 | C, 49.90%; H, 5.52%; N, 7.94% | C, 49.86%; H, 5.56%; N, 7.92% |
| Example 18 | Compound 129 | C, 52.12%; H, 6.07%; N, 7.44% | C, 52.09%; H, 6.11%; N, 7.40% |
| Example 19 | Compound 133 | C, 51.39%; H, 5.98%; N, 7.34% | C, 51.32%; H, 6.01%; N, 7.29% |
| Example 20 | Compound 135 | C, 50.15%; H, 5.70%; N, 7.31% | C, 50.11%; H, 5.75%; N, 7.27% |
| Example 21 | Compound 156 | C, 37.82%; H, 4.18%; N, 6.01% | C, 37.79%; H, 4.21%; N, 5.97% |
| Example 22 | Compound 157 | C, 37.82%; H, 4.18%; N, 6.01% | C, 37.78%; H, 4.21%; N, 5.97% |
| Example 23 | Compound 179 | C, 40.11%; H, 4.67%; N, 5.73% | C, 40.08%; H, 4.71%; N, 5.69% |
| Example 24 | Compound 183 | C, 39.67%; H, 4.62%; N, 5.67% | C, 39.64%; H, 4.67%; N, 5.62% |
| Example 25 | Compound 185 | C, 38.75%; H, 4.40%; N, 5.65% | C, 38.72%; H, 4.46%; N, 5.61% |

Example 24

Synthesis of Compound 183

Into 40 ml of DMF was completely dissolved 5 g of bis(4-di(n-butyl)aminophenyl)-4-di(n-butyl)amino-2-methoxyphenylamine, and the solution was heated and stirred at 60° C. To this was added 12 g of tris(trifluoromethanesulfonyl) methyl silver, and the mixture was heated and stirred at 60° C. for 3 hours. The reaction solution was filtered to remove insoluble components, 200 ml of water was added to the reaction solution, and precipitated crystal was collected by filtration. Resulting crystal was washed with water, and dried to obtain 7.5 g (88%) of a target compound 183.

When a mass spectrum was measured, $M^+$ was 657. When an absorption spectrum was measured, a maximum absorption wavelength was λmax=924 nm (dichloromethane).

Results of elemental analysis are shown in Table 9.

<Assessment>

Triarylamine derivatives according to the present invention obtained above, and triarylamine derivatives of Comparative Examples shown in the following in Table 10 were subjected to the following assessment.

(Sample for Assessment)

Into 25 ml of dichloromethane were dissolved 2.5 g of PMMA, and 0.125 g of the triarylamine derivative, and the solution was coated on a 100 μm-thick PET film. This was dried at 80° C. for 2 hours under reduced pressure to prepare a sample for assessment having a thickness of from 2 to 3 μm. The sample for assessment contained the triarylamine derivative at 5% by weight based on PMMA.

(Heat Resistance)

The sample for assessment obtained above was heat-treated at 80° C. for 400 hours. The absorbance of the assessment sample at the maximum absorption wavelength of the triarylamine derivative (colorant) was measured, and a colorant residual rate (%) was obtained as a ratio of the absorbance after heat treatment relative to the absorbance before heat treatment. Results are shown in Table 10.

(Wet Heat Resistance)

The sample for assessment obtained above was subjected to wet heat treatment at 60° C. and a relative humidity of 90% for 200 hours. The absorbance of the assessment sample at the maximum absorption wavelength of the triarylamine derivative (colorant) was measured, and a colorant residual rate (%) was obtained as a ratio of the absorbance after wet heat treatment relative to the absorbance before wet heat treatment. Results are shown in Table 10.

(Light Resistance)

The sample for assessment obtained above was irradiation-treated for 170 hours with a xenon lamp (170 thousands lux, using an UV cut filter). The absorbance of the assessment sample at the maximum absorption wavelength of the triarylamine derivative (colorant) was measured, and a colorant residual rate (%) was obtained as a ratio of the absorbance after irradiation treatment relative to the absorbance before irradiation treatment. Results are shown in Table 10.

(Solubility)

Solubility (w/v %) of the triarylamine derivative in 2-butanone (MEK) was measured, Results are shown in Table 10.

TABLE 10

| Triarylamine Derivative | Heat Resistance | Wet Heat Resistance | Light Resistance | Solubility (w/v) | Remarks |
| --- | --- | --- | --- | --- | --- |
| 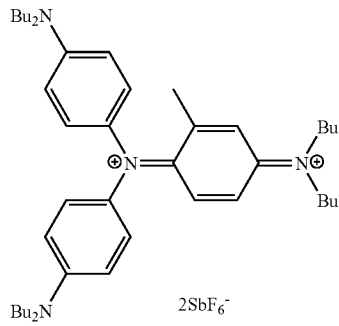 | 82% | 48% | 98% | 23% | Example Compound 28 |
| 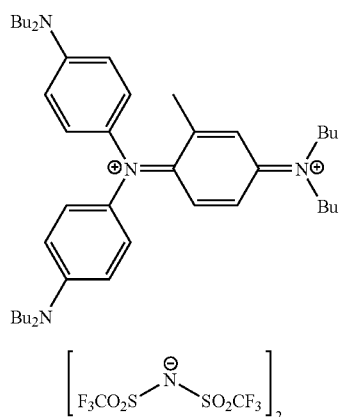 | 87% | 89% | 99% | 32% | Example Compound 79 |
| 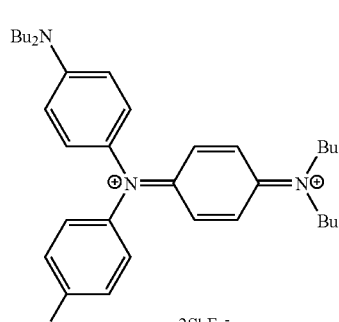 | 80% | 45% | 98% | 16% | Comparative Example |

From Table 10, it is seen that the triarylamine derivatives according to the invention are near infrared absorbing triarylamine derivatives excellent in light resistance, wet heating resistance and solubility.

In addition, it is seen that a maximum absorption wavelength may be changed by making one group among $R^{113}$ to $R^{116}$, and $R^{123}$ to $R^{126}$ different from the other groups.

According to the invention, a near infrared absorbing triarylamine derivative which is good in light resistance, wet heat resistance and solubility can be provided.

All publications, patent applications, and technical standards mentioned in this specification are herein incorporated by reference to the same extent as if each individual publication, patent application, or technical standard was specifically and individually indicated to be incorporated by reference.

What is claimed is:

1. A triarylamine derivative represented by the following Formula (I):

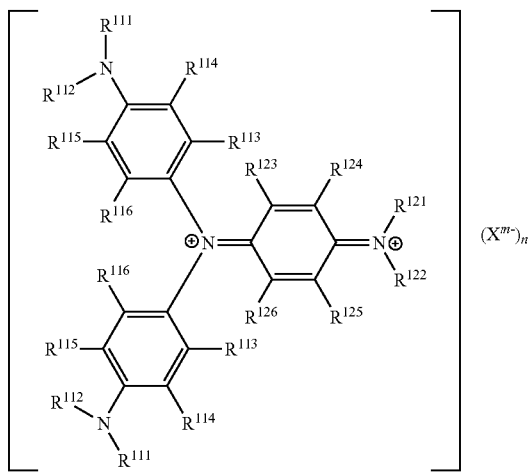

Formula (I)

wherein, in Formula (I): $R^{111}$ and $R^{112}$ each independently represent a hydrogen atom, an aliphatic group or an aromatic group, $R^{121}$ and $R^{122}$ each independently represent a hydrogen atom, a substituted or unsubstituted alkyl group, a substituted or unsubstituted alkenyl group, or a substituted or unsubstituted alkynyl group, $R^{113}$, $R^{114}$, $R^{115}$, $R^{116}$, $R^{123}$, $R^{124}$, $R^{125}$ and $R^{126}$ each independently represent a hydrogen atom, a halogen atom, an alkyl group, an alkenyl group, an alkynyl group, an aryl group, a cyano group, a hydroxy group, a carboxy group, an alkoxy group, an aryloxy group, a silyloxy group, an acyloxy group, a carbamoyloxy group, an alkoxycarbonyloxy group, an aryloxycarbonyloxy group, an amino group, an acylamino group, an aminocarbonylamino group, an alkoxycarbonylamino group, an aryloxycarbonylamino group, a sulfamoylamino group, an alkyl or aryl-sulfonyl amino group, a mercapto group, an alkylthio group, an arylthio group, a sulfamoyl group, a sulfo group, an alkyl- or aryl-sulfinyl group, an alkyl- or aryl-sulfonyl group, an acyl group, an aryloxycarbonyl group, an alkoxycarbonyl group, a carbamoyl group, an imido group, a phosphino group, a phosphinyl group, a phosphinyloxy group, a phosphinylamino group, or a silyl group, provided that at least one pair among $R^{111}$ and $R^{121}$, $R^{112}$ and $R^{122}$, $R^{113}$ and $R^{123}$, $R^{114}$ and $R^{124}$, $R^{115}$ and $R^{125}$, and $R^{116}$ and $R^{126}$ includes two different groups; at least one ring may be formed by mutual bonding in at least one pair among $R^{111}$ and $R^{112}$, $R^{111}$ and $R^{114}$, $R^{113}$ and $R^{114}$, $R^{113}$ and $R^{123}$, $R^{123}$ and $R^{124}$, $R^{121}$ and $R^{124}$, $R^{121}$ and $R^{122}$, and two $R^{116}$s which are respectively bound to different phenyl groups;

$X^{m-}$ represents an m-valent anion; m and n represent 1 or 2; and a product of m and n is 2.

2. The triarylamine derivative according to claim 1, wherein at least one group among $R^{111}$, $R^{112}$, $R^{121}$ and $R^{122}$ in Formula (I) is different from a remainder of these groups.

3. The triarylamine derivative according to claim 1, wherein at least one group among $R^{113}$, $R^{114}$, $R^{115}$, $R^{116}$, $R^{123}$, $R^{124}$, $R^{125}$ and $R^{126}$ in Formula (I) is different from a remainder of these groups.

4. The triarylamine derivative according to claim 1, wherein $R^{111}$, $R^{112}$, $R^{121}$ and $R^{122}$ each independently represent a substituted or unsubstituted alkyl group having a total carbon number of from 2 to 6.

5. The triarylamine derivative according to claim 1, wherein at least one ring is formed by mutual bonding in at least one pair among $R^{111}$ and $R^{112}$, $R^{111}$ and $R^{114}$, $R^{113}$ and $R^{114}$, $R^{113}$ and $R^{123}$, $R^{123}$ and $R^{124}$, $R^{121}$ and $R^{124}$, $R^{121}$ and $R^{122}$, and two $R^{116}$s which are respectively bound to different phenyl groups.

6. The triarylamine derivative according to claim 1, wherein $X^{m-}$ in Formula (I) represents a perchlorate ion, a hexafluoroantimonate ion, a hexafluorophosphate ion, a tetrafluoroborate ion or an anion represented by any of the following Formulae (II) to (IV):

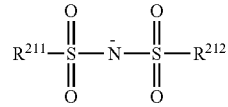

Formula (II)

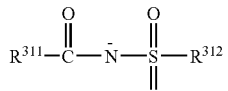

Formula (III)

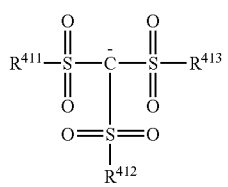

Formula (IV)

wherein, in Formulae (II) to (IV), $R^{211}$, $R^{212}$, $R^{311}$, $R^{312}$, $R^{411}$, $R^{412}$ and $R^{413}$ each independently represent an aliphatic group, an aromatic group or a heterocyclic group.

7. The triarylamine derivative according to claim 6, wherein $X^{m-}$ in Formula (I) represents an anion represented by any of Formula (II) to Formula (IV), and $R^{211}$, $R^{212}$, $R^{311}$, $R^{312}$, $R^{411}$, $R^{412}$ and $R^{413}$ each independently represent an aliphatic group having a halogen atom, an aromatic group having a halogen atom or a heterocyclic group having a halogen atom.

8. The triarylamine derivative according to claim 7, wherein $R^{211}$, $R^{212}$, $R^{311}$, $R^{312}$, $R^{411}$, $R^{412}$ and $R^{413}$ in Formulae (II) to (IV) represent an aliphatic group having a fluorine atom, an aromatic group having a fluorine atom, or a heterocyclic group having a fluorine atom.

9. The triarylamine derivative according to claim 6, wherein $R^{211}$, $R^{212}$, $R^{311}$, $R^{312}$, $R^{411}$, $R^{412}$ and $R^{413}$ each independently represent an alkyl group having 1 to 6 carbon atoms.

10. The triarylamine derivative according to claim 6, wherein $R^{111}$ and $R^{112}$ each independently represent a hydrogen atom, an alkyl group, or an aryl group, $R^{121}$ and $R^{122}$ each independently represent a hydrogen atom or an alkyl group, one or two groups selected from $R^{111}$, $R^{112}$, $R^{121}$ and $R^{122}$ each independently represent a different group from a remainder of these groups, $R^{211}$, $R^{212}$, $R^{311}$, $R^{312}$, $R^{411}$, $R^{412}$ and $R^{413}$ each independently represent an alkyl group, an aryl group, an alkenyl group, an alkynyl group or a heterocyclic group, and $X^{m-}$ represents a perchlorate ion, a hexafluoroantimonate ion, a hexafluorophosphate ion, a tetrafluoroborate ion, or an anion represented by any of Formulae (II) to (IV).

11. The triarylamine derivative according to claim 6, wherein $R^{111}$ and $R^{112}$ each independently represent a hydrogen atom, an alkyl group, or an aryl group, $R^{121}$ and $R^{122}$ each independently represent a hydrogen atom or an alkyl group, $R^{211}$, $R^{212}$, $R^{311}$, $R^{312}$, $R^{411}$, $R^{412}$ and $R^{413}$ each independently represent an alkyl group, an aryl group, an alkenyl group, an alkynyl group or a heterocyclic group, one group selected from $R^{211}$, $R^{212}$, $R^{311}$, $R^{312}$, $R^{411}$, $R^{412}$ and $R^{413}$ is a different group from a remainder of these groups, and $X^{m-}$ represents a perchlorate ion, a hexafluoroantimonate ion, a hexafluorophosphate ion, a tetrafluoroborate ion, or an anion represented by any of Formulae (II) to (IV).

12. The triarylamine derivative according to claim 6, wherein $R^{111}$, $R^{112}$, $R^{121}$ and $R^{122}$ each independently represent an alkyl group, one or two groups selected from $R^{111}$, $R^{112}$, $R^{121}$ and $R^{122}$ each independently represent a different group from a remainder of these groups, $R^{211}$, $R^{212}$, $R^{311}$, $R^{312}$, $R^{411}$, $R^{412}$ and $R^{413}$ each independently represent a hydrogen atom, and $X^{m-}$ is an anion represented by any one of Formulae (II) to (IV).

13. The triarylamine derivative according to claim 6, wherein $R^{111}$, $R^{112}$, $R^{121}$ and $R^{122}$ each independently represent an alkyl group, $R^{211}$, $R^{212}$, $R^{311}$, $R^{312}$, $R^{411}$, $R^{412}$ and $R^{413}$ each independently represent a hydrogen atom, an alkyl group, an aryl group, an alkoxy group, a cyano group, or an acyl group, one group selected from $R^{211}$, $R^{212}$, $R^{311}$, $R^{312}$, $R^{411}$, $R^{412}$ and $R^{413}$ is a different group from a remainder of these groups, and $X^{m-}$ is an anion represented by any of Formula (II) to Formula (IV).

14. The triarylamine derivative according to claim 1, wherein $R^{121}$ and $R^{122}$ each independently represent a substituted or unsubstituted alkyl group having a total carbon number of from 2 to 6.

* * * * *